United States Patent
Crainich et al.

(10) Patent No.: US 9,566,101 B2
(45) Date of Patent: Feb. 14, 2017

(54) DEVICES AND METHODS FOR VERTEBROSTENTING

(75) Inventors: Lawrence Crainich, Charlestown, NH (US); Andrew R. Sennett, Hanover, MA (US); Joseph Trabka, Charlestown, NH (US)

(73) Assignee: GLOBUS MEDICAL, INC., Audubon, PA (US)

( * ) Notice: Subject to any disclaimer, the term of this patent is extended or adjusted under 35 U.S.C. 154(b) by 1009 days.

(21) Appl. No.: 12/688,418

(22) Filed: Jan. 15, 2010

(65) Prior Publication Data

US 2010/0121332 A1    May 13, 2010

Related U.S. Application Data

(62) Division of application No. 11/957,022, filed on Dec. 14, 2007, now Pat. No. 9,237,916.

(60) Provisional application No. 60/875,114, filed on Dec. 15, 2006, provisional application No. 60/875,173, filed on Dec. 15, 2006.

(51) Int. Cl.
   *A61B 17/04* (2006.01)
   *A61B 17/88* (2006.01)
   *A61B 17/16* (2006.01)

(52) U.S. Cl.
   CPC ........... *A61B 17/8805* (2013.01); *A61B 17/16* (2013.01); *A61B 17/1617* (2013.01); *A61B 17/1637* (2013.01); *A61B 17/1642* (2013.01); *A61B 17/1671* (2013.01); *A61B 17/8808* (2013.01); *A61B 17/8816* (2013.01); *A61B 17/8822* (2013.01); *A61B 17/88* (2013.01); *A61B 17/885* (2013.01); *A61B 17/8858* (2013.01)

(58) Field of Classification Search
   CPC ............................ A61B 17/88; A61B 17/1757
   USPC .......... 606/79–85, 86 R, 167–169, 171–172, 606/175, 300–321; 600/139–152
   See application file for complete search history.

(56) References Cited

U.S. PATENT DOCUMENTS

| | | | | |
|---|---|---|---|---|
| 5,448,989 A | * | 9/1995 | Heckele | 600/142 |
| 5,772,578 A | * | 6/1998 | Heimberger et al. | 600/139 |
| 6,102,920 A | * | 8/2000 | Sullivan et al. | 606/147 |
| 6,248,062 B1 | * | 6/2001 | Adler et al. | 600/204 |
| 6,575,979 B1 | * | 6/2003 | Cragg | 606/86 R |
| 6,743,239 B1 | * | 6/2004 | Kuehn et al. | 606/139 |
| 7,320,700 B2 | * | 1/2008 | Cooper et al. | 606/205 |
| 2004/0106940 A1 | * | 6/2004 | Shaolian et al. | 606/170 |
| 2007/0167680 A1 | * | 7/2007 | Miyamoto et al. | 600/106 |
| 2007/0232858 A1 | * | 10/2007 | Macnamara | A61B 1/0052 600/149 |

\* cited by examiner

*Primary Examiner* — Matthew Lawson

(57) ABSTRACT

The invention relates to a method of creating a curvilinear cavity within a vertebral body or other body structure. The invention also relates to devices that may be used to perform the steps to create the curvilinear cavity. One such device is a curved drill including a spring assembly that controls the curvature of the drill. The spring assembly can cooperate with a feed screw to assist in curving the drill. The curved drill can be provided through a cannula.

20 Claims, 27 Drawing Sheets

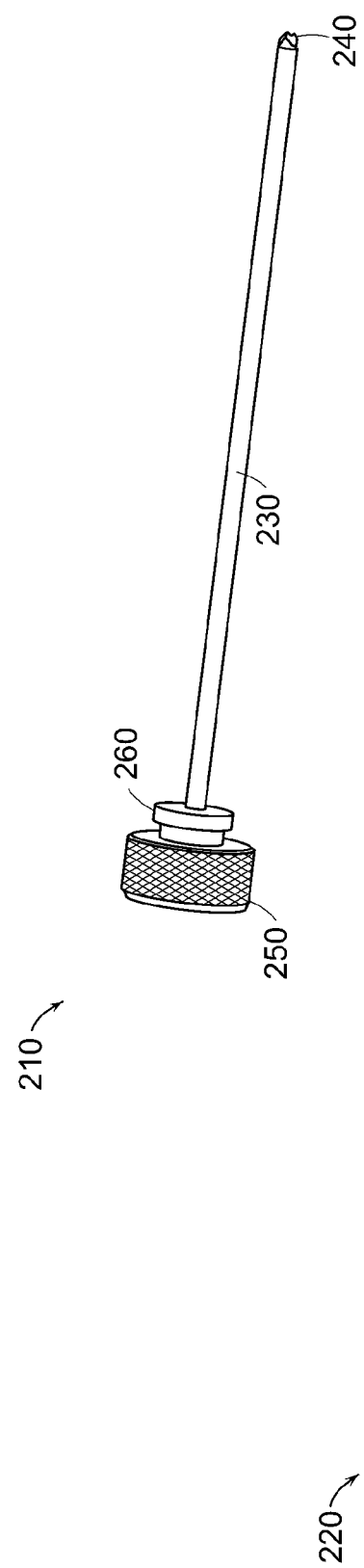
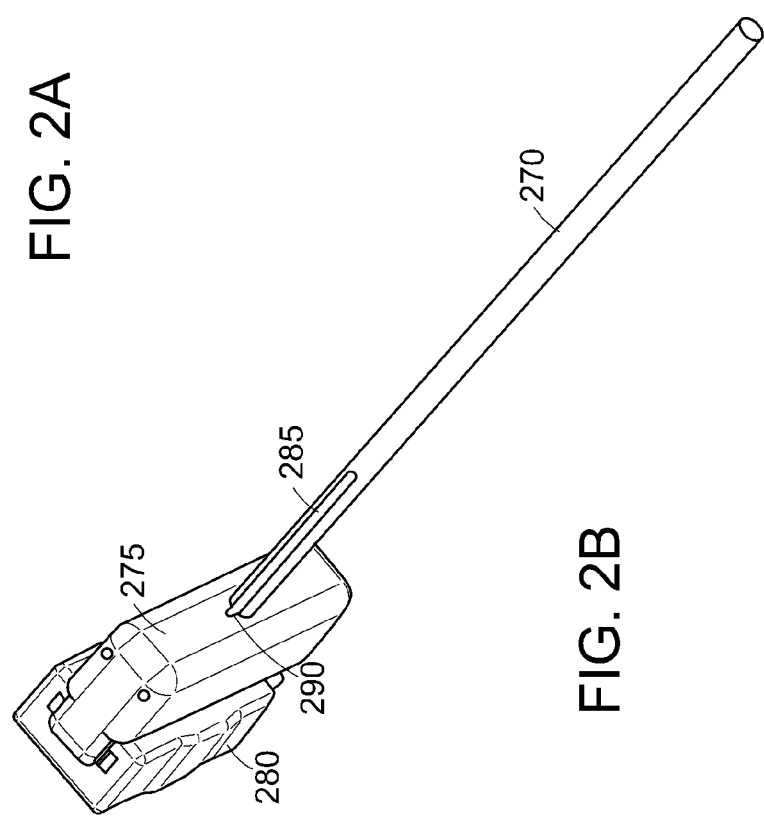
FIG. 2A
FIG. 2B

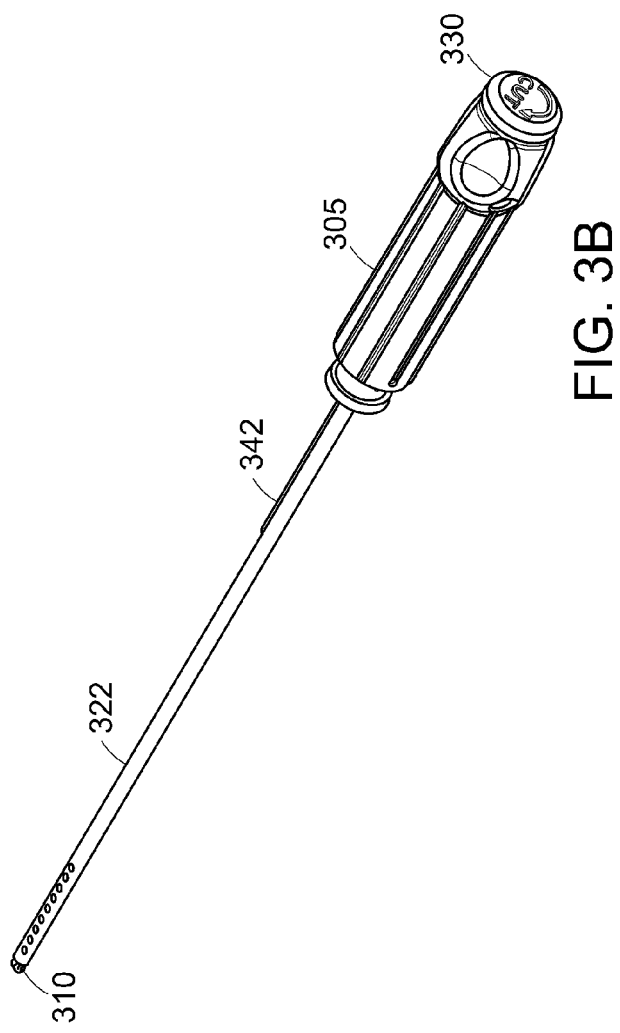
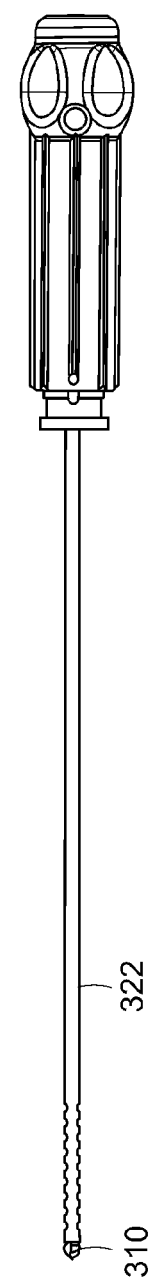
FIG. 3B
FIG. 3C
FIG. 3D

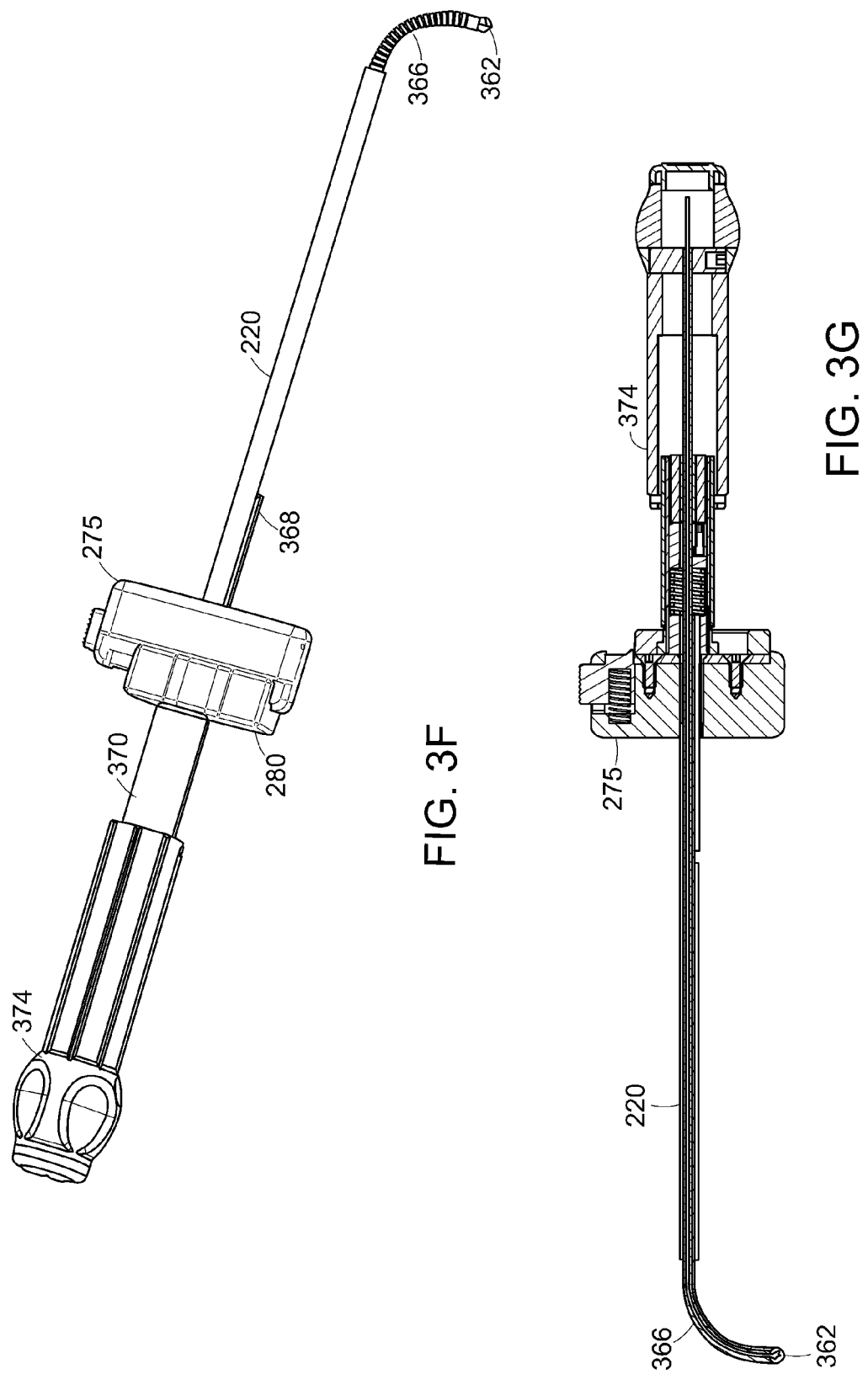

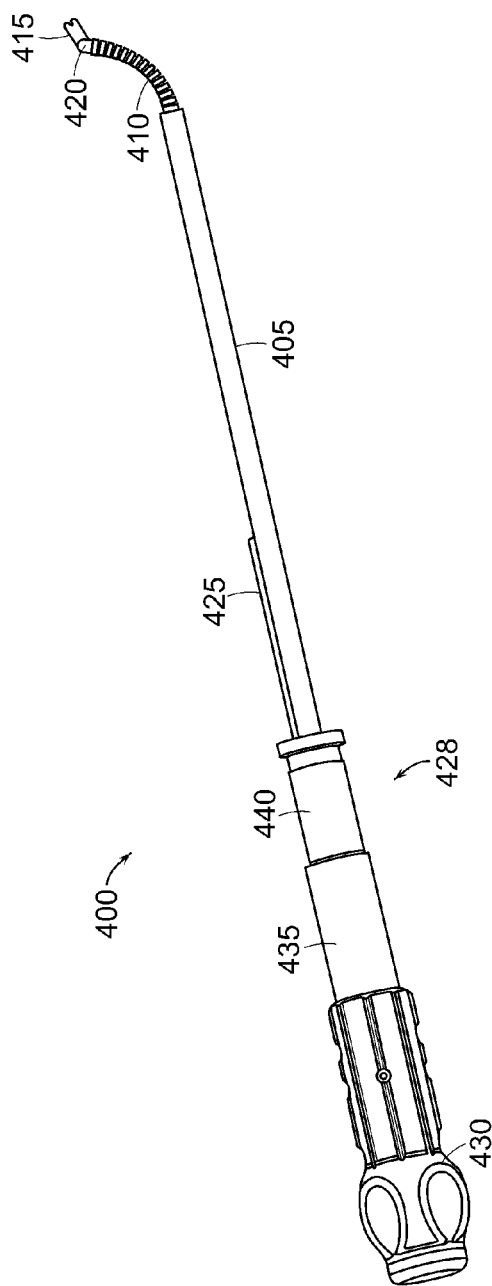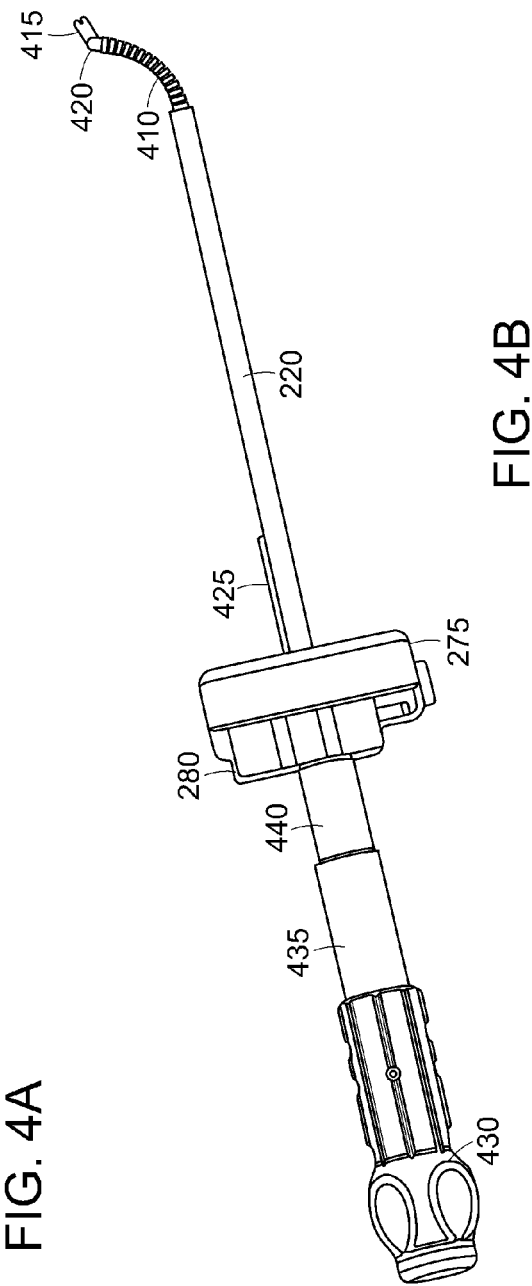
FIG. 4A
FIG. 4B

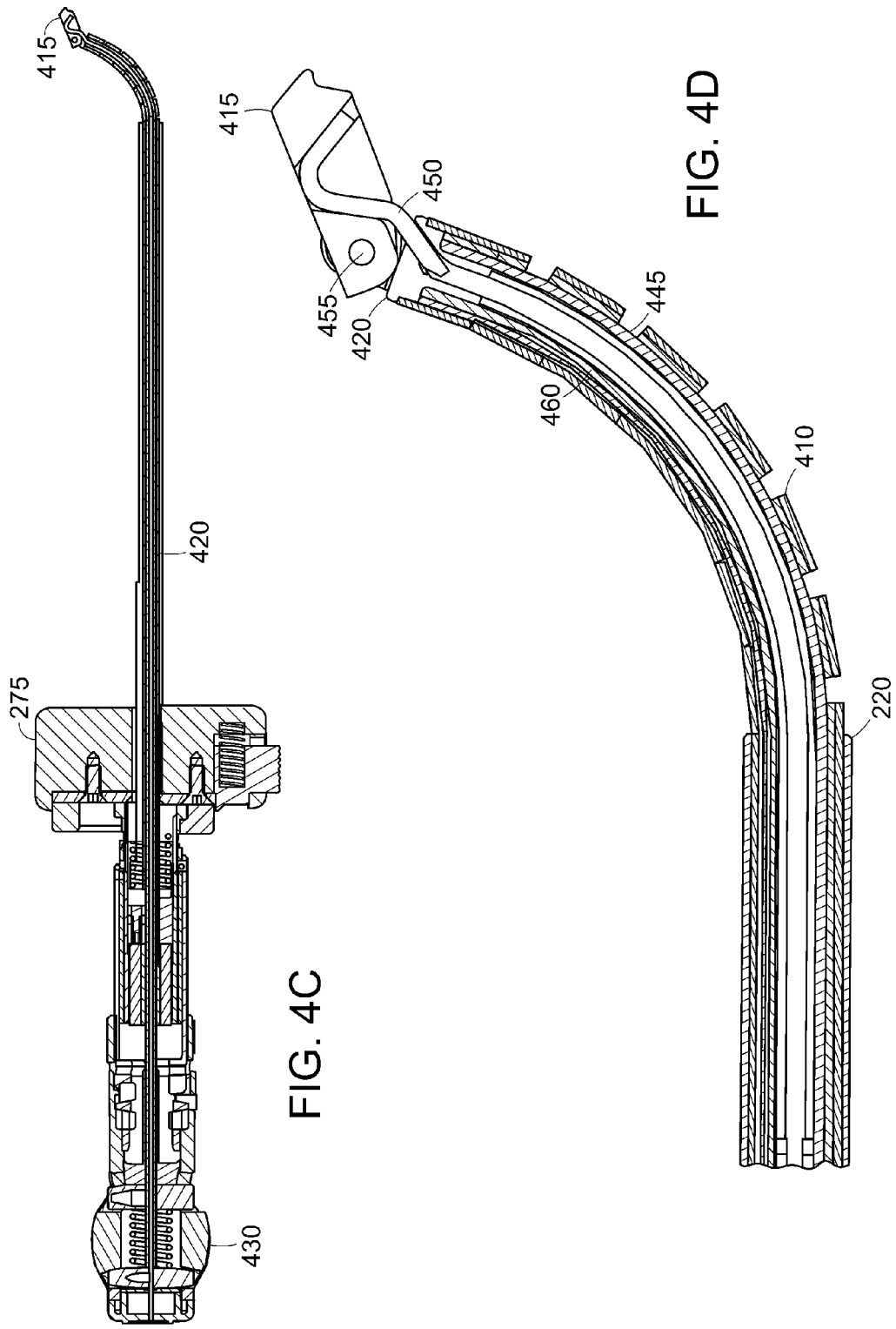

DEVICES AND METHODS FOR VERTEBROSTENTING

CROSS-REFERENCE TO RELATED APPLICATIONS

This application is a divisional of U.S. patent application Ser. No. 11/957,022, filed Dec. 14, 2007, and is related to U.S. patent application Ser. No. 11/957,039, filed Dec. 14, 2007, the disclosures of which are being incorporated herein by reference in their entireties. This application further claims priority to and the benefit of U.S. provisional patent application Ser. No. 60/875,114 filed Dec. 15, 2006, and U.S. provisional patent application Se. No. 60/875,173 filed Dec. 15, 2006, the disclosures of which are being incorporated herein by reference in their entirety.

FIELD OF THE INVENTION

The present invention relates generally to the field of orthopedic devices to treat fractured bone in the spine, and more particularly to an orthopedic instrument and implant system that can be used to facilitate bone cement treatment of a vertebral compression fracture.

BACKGROUND OF THE INVENTION

There are many disease states that cause bone defects in the spinal column. For instance, osteoporosis and other metabolic bone conditions weaken the bone structure and predispose the bone to fracture. If not treated, certain fractures and bone defects of the vertebral body may produce intolerable pain, and may lead to the development of deformity and severe medical complications.

Bone weakening may also result from benign or malignant lesions of the spinal column. Tumors often compromise the structural integrity of the bone and thus require surgical stabilization and repair of defects with biocompatible materials such as bone grafts or cements. Bone tumors of the spine are relatively common, and many cause vertebral compression fracture.

More than 700,000 osteoporotic compression fractures of the vertebrae occur each year in the United States—primarily in the elderly female population. Until recently, treatment of such fractures was limited to conservative, non-operative therapies such as bed rest, bracing, and medications.

One surgical technique for treating vertebral compression fracture can include injecting or filling the fracture bone or bone defect with biocompatible bone cement. A relatively new procedure known as "vertebroplasty" was developed in the mid 1980's to address the inadequacy of conservative treatment for vertebral body fracture. This procedure involves injecting radio-opaque bone cement directly into a fracture void, through a minimally invasive cannula or needle, under fluoroscopic control. The cement is pressurized by a syringe or similar plunger mechanism, thus causing the cement to fill the void and penetrate the interstices of a broken trabecular bone. Once cured, the cement stabilizes the fracture and eliminates or reduces pain. Bone cements are generally formulations of non-resorbable biocompatible polymers such as PMMA (polymethylmethacrylate), or resorbable calcium phosphate cements which allow for the gradual replacement of the cement with living bone. Both types of bone cements have been used successfully in the treatment of bone defects secondary to compression fractures of the vertebral body.

One clinical issue associated with vertebroplasty is containment of the cement within the margins of the defect. For instance, an osteoporotic compression fracture usually compromises portions of the cortical bone creating pathways to cement leakage. Thus, there is a risk of cement flowing beyond the confines of the bone into the body cavity. Cement leakage into the spinal canal, for instance, can have grave consequences to the patient.

Yet another significant risk associated with vertebroplasty is the injection of cement directly into the venous system, since the veins within the vertebral body are larger than the tip of the needle used to inject the cement. A combination of injection pressure and inherent vascular pressure may cause unintended uptake of cement into the pulmonary vessel system, with potentially disastrous consequences including embolism to the lungs.

One technique which has gained popularity in recent years is a modified vertebroplasty technique in which a "balloon tamp" is inserted into the vertebral body via a cannula approach to expand or distract the fractured bone and create a void within the cancellous structure. Balloon tamps are inflated using pressurized fluid such as saline solution. The inflation of a balloon membrane produces radial forces on the surface of the membrane and forms a cavity in the bone. When deflated and removed, the membrane leaves a cavity that is subsequently filled with bone cement. The formation of a cavity within the bone allows for the injection of more viscous cement material, which may be relatively less prone to leakage.

In certain instances, such as the treatment of acute or mobile fractures, the balloon is also effective at "reducing" the fracture and restoring anatomic shape to a fractured body. In particular, balloon dilatation in bone is maximally effective if the balloon device is targeted inferior to, or below, the fracture plane. In this instance, the balloon dilatation may distract, or lift, a fracture bone fragment, such as the vertebral body endplate.

In other instances, such as chronic or partially healed fractures, balloons are less effective at "reducing" the fracture because radial forces are insufficient. Often the bone in an incompletely healing fracture is too dense and strong, and requires more aggressive cutting treatment, such as a drill or reamer tool to create a sufficient cavity. In these more challenging cases, the ability to inject bone cement into a cavity created by a balloon or a reamer in the vicinity of the fracture is typically sufficient to stabilize the bone and relieve pain, even in the absence of fracture reduction.

One limitation to the use of such methods has been the difficulty in targeting the location at which the cavity should be created. Known techniques require access to the vertebral body using straight cutting and reaming tools which are only able to access a limited region of the vertebral body being treated, generally only within one side of the vertebral body. A cavity created using these techniques can only treat one side of a vertebral body being targeted, resulting in an uneven distribution of bone cement that cannot completely stabilize the vertebral body. As a result, multiple entry points on different sides of the vertebral body are generally required in order to provide a symmetrical distribution of bone cement around a central axis of the vertebral body. These multiple entry points significantly increase the time necessary for the procedure, the portion of the body being treated, and the amount of bone cement being injected, and, as such, can significantly increase the risks associated with treatment of a patient, as well as costs.

SUMMARY OF THE INVENTION

The present invention is directed towards novel methods and devices for preparing a cavity in bone. The methods and devices disclosed herein can allow a cavity to be created in a vertebral body along a curvilinear pathway, allowing for a substantially symmetrical distribution of bone cement over a central vertical axis of a vertebral body. This can allow a vertebral body to be successfully and completely stabilized from a single surgical access point and using a single stent device.

In one embodiment of the invention, a stent can include a multifilament co-braided shaped structure which is collapsible to an elongated tubular shape suitable to fit within a tubular sheath assembled to a novel delivery catheter. The outer wall of the stent is impregnated in preferred regions with a polymer to form a thicker, relatively less permeable wall. The polymer impregnated co-braided wall is further perforated with holes or slots in preferred locations. An example cement directing stent for use with this invention is disclosed in U.S. Patent Publication No. 2005/0261781 A1 to Sennett et al., the disclosure of which is incorporated by reference herein in its entirety. The stent geometry is optimized to fit within a reamed or balloon-expanded cavity located approximately within the anterior ⅔ of a vertebral body. The cavity is formed by a sequential method using a number of specifically designed instruments.

One aspect of the invention includes a method of forming a curvilinear void in bony structure. The method can include the steps of, accessing a bony structure with a cannula, inserting a distal end of a drill device through the cannula and into the bony structure, manipulating the distal end of the drill device to create a curvilinear void in the bony structure, and removing the distal end of the drill device from the bony structure and the cannula.

In one embodiment of the invention, the step of manipulating of the distal end of the drill device can include a simultaneous rotation and curvilinear translation of the distal end of the drill device. The cannula can be substantially straight or include a curvature. The drilling device can include a flexible drill shaft assembly. The flexible drill shaft assembly can include a sharp cutting tip, a flexible rotatable drive shaft coupled to the tip, and a flexible, moveable and non-rotatable housing.

In one embodiment, the step of manipulating the distal end of the drill device can include inducing a curvature in the distal end of the flexible drill shaft assembly. In one embodiment, the flexible drill shaft assembly can include a lever and cam sub assembly for varying a force used to apply the curvature to the distal end of the flexible drill shaft assembly.

One embodiment of the invention can also include the steps of moving the lever to a first position to reduce the force on the distal end of the flexible drill shaft assembly prior to inserting the distal end of the drill device through the cannula, and moving the lever to a second position to increase the force on the distal end of the flexible drill shaft assembly after inserting the distal end of the drill device through the cannula.

One embodiment of the invention can also include the step of moving the lever to the first position to reduce the force on the distal end of the flexible drill shaft assembly prior to removing the distal end of the drill device from the cannula.

In one embodiment, the drilling device can include a locking feature. The method can further include locking the drill device into the cannula using the locking feature prior to forming the void, and unlocking the drill device from the cannula after forming the void and prior to removing the distal end of the drill device. In one embodiment, the drill device can be manipulated in response to a rotation of an element at a proximal end of the drill device.

One aspect of the invention can include a method of enlarging a curvilinear void created in a bony structure. The method can include the steps of inserting a distal end of a reamer device through a cannula and into a curvilinear void created in a bony structure, for example by the drill device, deploying a reaming element within the curvilinear void, wherein the reaming element is coupled to the distal end of a reamer device, manipulating the reaming element to enlarge the curvilinear void, returning the reaming element to an undeployed position, and removing the distal end of the reamer device from the bony structure and the cannula.

In one embodiment of the invention, the reamer device can include a flexible reamer shaft assembly coupled to the reaming element. The flexible reamer shaft assembly can include a flexible rotatable drive shaft coupled to the reaming element, and a flexible, moveable and non-rotatable housing. The reaming element may be deployed by a rotation of an element at a proximal end of the reamer device. The reaming element may be also be manipulated by a rotation of an element at a proximal end of the reamer device.

In one embodiment, the step of deploying a reaming element within the curvilinear void can include inducing a curvature in a distal end of the flexible reamer shaft assembly. In one embodiment, the flexible reamer shaft assembly can include a lever and cam sub assembly for varying a force used to apply the curvature to the distal end of the flexible reamer shaft assembly.

One embodiment of the invention can also include the steps of moving the lever to a first position to reduce the force on the distal end of the flexible reamer shaft assembly prior to inserting the distal end of the reamer device through the cannula, and moving the lever to a second position to increase the force on the distal end of the flexible reamer shaft assembly after inserting the distal end of the drill device through the cannula.

One embodiment of the invention can also include the step of moving the lever to the first position to reduce the force on the distal end of the flexible reamer shaft assembly prior to removing the distal end of the reamer device from the cannula.

In one embodiment, the step of manipulating the reaming element can include a simultaneous rotation and curvilinear translation of the reaming element, tracing a generally helical path. The distal end of the reamer device can initially be inserted to a distal end of the curvilinear void. The curvilinear translation of the reaming element can be in a retrograde direction, or in an anterior direction. The reaming element can include a blade.

One aspect of the invention can include a method of deploying a stent within an enlarged curvilinear void created in a bony structure. The method can include the step of inserting a stent catheter assembly through a cannula and into a curvilinear void created in a bony structure, wherein the stent catheter assembly can include a proximal deployment mechanism, an internal flexible guidewire, a multifilament braided, polymer impregnated, self-expanding, cement-directing stent collapsed on the distal end of the guidewire and restrained in a collapsed condition by a tubular polymer sheath, and connectably attached to the distal end of the deployment mechanism by a hollow tube assembly.

The method can further include the steps of deploying the self-expanding cement directing stent by slideably uncovering the tubular sheath to release the stent to expand within the enlarged void within the bony structure, removing the internal flexible guidewire, attaching a cement filled cement injecting syringe to the proximal deployment mechanism, injecting cement into the proximal deployment mechanism through the hollow tube assembly into the stent, compacting the cement to cause the complete filling of the stent interior, terminating the filling when the volume of cement injected meets or exceeds the nominal interior volume of the expanded stent, and releasing the stent from the hollow tube assembly.

One aspect of the invention can include a method of forming a void in bone on a curvilinear axis. The method can include the steps of accessing a bony structure with a cannula and inserting a telescoping tamp device into the cannula. The telescoping tamp device can include a flexible shaft assembly, comprising internal elastic curved wire and an outer hollow slotted tube concentric to, and secured to, the internal elastic curved wire, and a telescoping tubular handle bonded internally to the internal wire, and externally to the outer hollow flexible slotted tube.

In one embodiment, the method can also include the steps of locking the telescoping tamp device into the cannula by a locking feature, creating a void in bone by advancing the internal elastic curved wire relative to the cannula to a preferred depth, advancing the hollow slotted tube over the internal elastic curved wire to a preferred depth to enlarge the void, and removing the telescoping device from the cannula.

In one embodiment, the method can further include the steps of inserting a reamer device into the cannula and extending the reamer device fully within the curvilinear void, deploying the retractable blade within the curvilinear void to enlarge the void, elongating the void along a curvilinear axis in a retrograde fashion by rotating a reamer device knob to cause the simultaneous rotation and curvilinear translation of the flexible reamer shaft assembly relative to the cannula along a generally helical path, retracting the retractable blade assembly to the undeployed position, and removing the reamer device from the enlarged void and the cannula. The reamer device can include a flexible reamer shaft assembly comprising a retractable blade subassembly in an undeployed position, a flexible rotatable drive shaft bonded to the subassembly, and a flexible, moveable and non-rotatable housing.

In one embodiment, the method can also include the steps of inserting a stent catheter assembly into the enlarged curvilinear void through the cannula, deploying a self-expanding cement directing stent by slideably uncovering the tubular sheath to expand the stent within the enlarged void within the bony structure, removing an internal flexible guidewire, attaching a cement filled cement injecting syringe to a proximal deployment mechanism, injecting cement into the proximal deployment mechanism through the hollow tube assembly into the stent, compacting the cement to cause the complete filling of the stent interior, terminating the filling when the volume of cement injected meets or exceeds the nominal interior volume of the expanded stent, and releasing the stent from the hollow tube assembly.

In one embodiment, the stent catheter assembly can include a proximal deployment mechanism, an internal flexible guidewire, a multifilament braided, and a polymer impregnated, self-expanding, cement-directing stent collapsed on the distal end of the guidewire, and restrained in a collapsed condition by a tubular polymer sheath, and connectably attached to the distal end of the deployment mechanism by a hollow tube assembly.

One aspect of the invention can include a method of forming a void in bone on a curvilinear axis. The method can include the steps of accessing a bony structure with a straight cannula, inserting a drill device comprising a flexible drill shaft assembly comprising a sharp cutting tip, a flexible rotatable drive shaft bonded to the tip, and a flexible, moveable and non-rotatable housing into the cannula, locking the drill device into the cannula by a locking feature, rotating a drill device knob to cause the simultaneous rotation and curvilinear translation of the flexible drill shaft assembly relative to the cannula to generally trace a helical path, and unlocking the drill device from the cannula, and removing the drill device from the bony structure and cannula.

In one embodiment, the method can also include the steps of inserting a balloon catheter device comprising a flexible catheter shaft assembly, a compliant balloon structure located on the distal end of the catheter assembly, and a filling valve connected at the proximal end of the catheter assembly, into the cannula and extending fully within the curvilinear void, inflating the balloon structure, deflating the balloon structure, and removing the balloon catheter device from the enlarged void and the cannula.

In one embodiment, the method can also include the step of inserting a stent catheter assembly into the enlarged curvilinear void through the cannula, the stent catheter assembly comprising a proximal deployment mechanism, an internal flexible guidewire, a multifilament braided, polymer impregnated, self-expanding, cement-directing stent collapsed on the distal end of the guidewire, restrained in a collapsed condition by a tubular polymer sheath, and connectably attached to the distal end of the deployment mechanism by a hollow tube assembly.

One embodiment can also include deploying the self-expanding cement directing stent by slideably uncovering the tubular sheath to expand the stent within the enlarged void within the bony structure, removing the internal flexible guidewire, attaching a cement filled cement injecting syringe to the proximal deployment mechanism, injecting cement into the proximal deployment mechanism through the hollow tube assembly into the stent, compacting the cement to cause the complete filling of the stent interior, terminating the filling when the volume of cement injected meets or exceeds the nominal volume of the expanded stent interior, and releasing the stent from the hollow tube assembly.

In one embodiment, the method can also include the steps of inserting a balloon catheter device comprising a flexible catheter shaft assembly, a compliant balloon structure formed on the distal end of the catheter assembly, and a filling valve connected at the proximal end of the catheter assembly, into the cannula and extending fully within the curvilinear void, inflating the balloon structure, deflating the balloon structure, removing the balloon catheter device from the enlarged void and the cannula, and filling the void with bone cement.

One aspect of the invention can include a method of forming a void in bone on a curvilinear axis. The method can include the steps of accessing a bony structure with a straight cannula, inserting a drill device comprising a flexible drill shaft assembly comprising a sharp cutting tip, a flexible rotatable drive shaft bonded to the tip, and a flexible, moveable and non-rotatable housing into the cannula, locking the drill device into the cannula by a locking feature, rotating a drill device knob to cause the simultaneous rotation and curvilinear translation of the flexible drill shaft assembly relative to the cannula to generally trace a helical path, unlocking the drill device from the cannula, and removing the drill device from the bony structure and the cannula.

In one embodiment, the method can also include the step of inserting a stent catheter assembly into the enlarged curvilinear void through the cannula. The stent catheter assembly can include a proximal deployment mechanism, an internal flexible guidewire, and a multifilament braided, polymer impregnated, self-expanding, cement-directing stent collapsed on the distal end of the guidewire, and restrained in a collapsed condition by a multi-lumen tubular polymer sheath, and connectably attached to the distal end of the deployment mechanism by a hollow tube assembly.

One embodiment can also include injecting saline under pressure into the outer lumen of the multi-lumen tubular polymer sheath causing the distal end of the outer wall of the sheath to expand radially, withdrawing saline from the outer lumen to cause the outer lumen to retract, deploying the self-expanding cement directing stent by slideably uncovering the retracted tubular sheath to expand the stent within the enlarged void within the bony structure, removing the internal flexible guidewire, attaching a cement filled cement injecting syringe to the proximal deployment mechanism, injecting cement into the proximal deployment mechanism through the hollow tube assembly into the stent, compacting the cement to cause the complete filling of the stent interior, terminating the filling when the volume of cement injected meets or exceeds the nominal volume of the expanded stent interior, and releasing the stent from the hollow tube assembly.

Another aspect of the invention can include an apparatus for forming a curvilinear void in bony structure. The apparatus can include a handle and a flexible drill shaft assembly extending from a distal end of the handle. The flexible drill shaft assembly can include a cutting tip located at a distal end of the flexible drill shaft assembly, a flexible rotatable drive shaft coupled to the tip, and a flexible, moveable and non-rotatable housing.

In one embodiment, the cutting tip is adapted to form the curvilinear void by simultaneous rotation and curvilinear translation of the cutting tip. In one embodiment, the flexible drill shaft assembly is adapted to form a curvature at a distal end thereof. One embodiment further includes a lever and cam sub assembly for varying a force used to apply the curvature. The lever can have a first position at which the force is less than at a second position of the lever.

Another aspect of the invention can include an apparatus for enlarging a curvilinear void created in a bony structure. The apparatus can include a handle and a flexible drill shaft assembly extending from a distal end of the handle. The flexible drill shaft assembly can include a pivotable reaming blade located at a distal end of the flexible drill shaft assembly, a flexible rotatable drive shaft coupled to the tip, and a flexible, moveable and non-rotatable housing.

In one embodiment, the reaming blade is adapted to pivot from a first position to a second position. In one embodiment, the reaming blade is adapted to form the curvilinear void by simultaneous rotation and curvilinear translation of the reaming blade. In one embodiment, the flexible drill shaft assembly is adapted to form a curvature at a distal end thereof. One embodiment further includes a lever and cam sub assembly for varying a force used to apply the curvature. The lever has a first position at which the force is less than at a second position of the lever.

Another aspect of the invention can include an apparatus for treating a vertebral body. The apparatus can include a handle, a flexible shaft assembly extending from a distal end of the handle, and a lever and cam sub assembly for varying a force used to apply a curvature to a distal end of the flexible shaft assembly. In one embodiment, the lever has a first position at which the force is less than at a second position of the lever.

The invention is also drawn to cannulas, drills, and reamers and components thereof adapted for use with any of the methods described above.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 2A is schematic perspective view of a trocar, used in accordance with one embodiment of the invention;

FIG. 2B is schematic perspective view of a cannula, in accordance with one embodiment of the invention;

FIG. 3B is a schematic perspective view of the drill assembly of FIG. 3A;

FIG. 3C is a schematic side view of the drill assembly of FIG. 3A;

FIG. 3D is a schematic end view of the drill assembly of FIG. 3A;

FIG. 3F is a schematic perspective view of the drill assembly of FIG. 3E inserted within a cannula, in accordance with one embodiment of the invention;

FIG. 3G is a sectional side view of the drill assembly of FIG. 3E inserted within a cannula;

FIG. 3I is an enlarged sectional side view of the proximal end of the drill assembly of FIG. 3E inserted within a cannula;

FIG. 4A is a schematic perspective view of a reamer assembly, in accordance with one embodiment of the invention;

FIG. 4B is a schematic perspective view of the reamer assembly of FIG. 4A inserted within a cannula, in accordance with one embodiment of the invention;

FIG. 4C is a sectional side view of the reamer assembly of FIG. 4A inserted within a cannula;

FIG. 4D is an enlarged sectional side view of the distal end of the reamer assembly of FIG. 4A;

DETAILED DESCRIPTION OF THE INVENTION

To maximize the effectiveness of balloon dilatation or bone cutting with a reamer, it would be beneficial to more effectively target the location within the bone prior to dilatation of the balloon. In the specific case of vertebral body fracture, there are anatomical challenges to targeting with minimally invasive instrumentation. Safe passage of instruments and balloon catheters from the posterior surgical approach is generally achieved through a straight cannula positioned within the pedicle of the vertebral body, or just lateral to the pedicle to avoid potentially dangerous penetration of the cannula in the spinal canal. This anatomically defined trajectory often does not align with, or target, the fracture within the vertebral body. Therefore, there are limitations in current techniques to effectively target the fracture.

There are numerous devices disclosed in the art to make the injection of cement into the vertebral body a safer procedure. One novel device, an implantable cement-directing stent device, is disclosed in U.S. Patent Publication No. 2005/0261781 A1 to Sennett et al., the disclosure of which is incorporated herein by reference in its entirety. The implantable cement-directing stent device provides a means to temporarily stabilize a fractured vertebral body after cavity creation during cement injection, while also directing the flow of cement anteriorly within the vertebral body to prevent unwanted cement flow near the spinal canal. This disclosure presents additional novel devices and methods of use to fully describe the technique of "vertebrostenting" to treat vertebral compression fracture using conventional stent devices or the improved stent device of Sennett et al.

Needle

In one embodiment of the invention, access to the vertebral body can be achieved using a pointed needle or wire to pierce the skin and underlying tissue and entering into the pedicle, a depression of the vertebral body, until the needle is held fast. The needle can then be pressed into the vertebral body until it is held firmly in place by the wall of the vertebral body. The needle can then become a guide for the placement of subsequent devices.

Figure 1A:
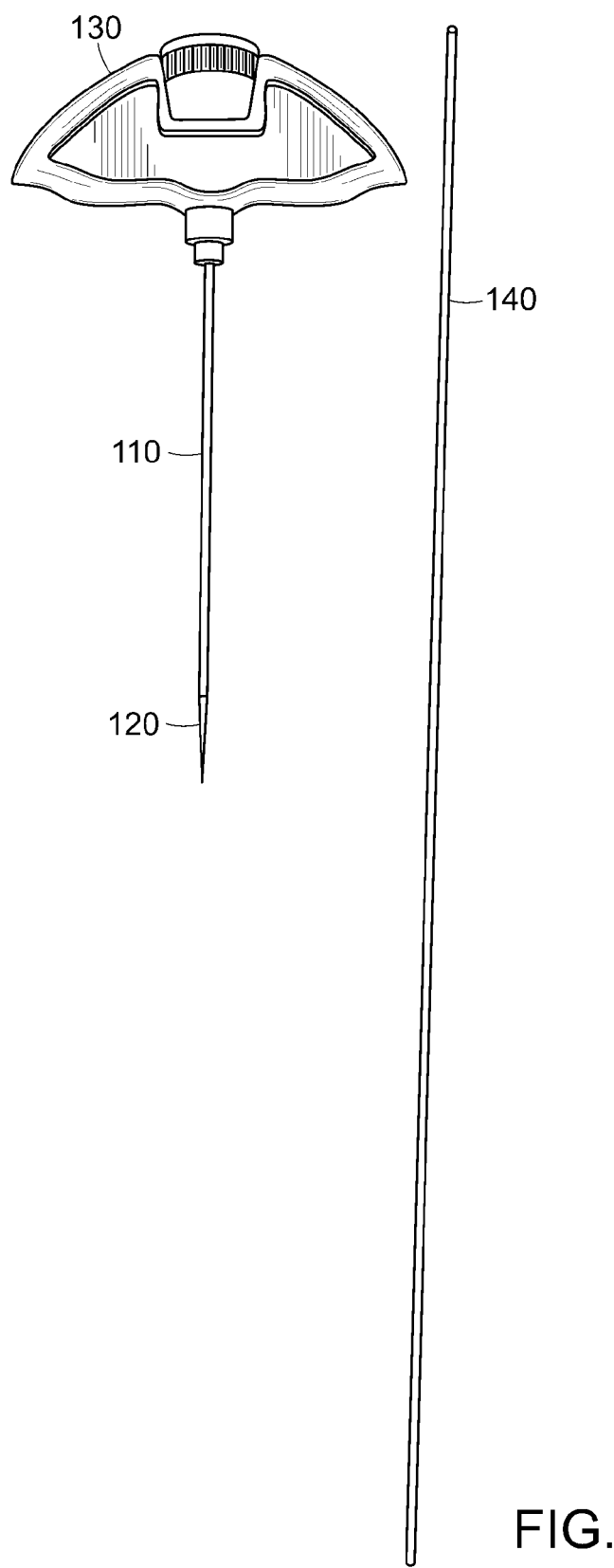
FIG. 1A is a schematic plan view of a Jamshidi needle and K-wire, used in accordance with one embodiment of the invention.

In an example embodiment of the invention, a Jamshidi needle and K-wire arrangement can be used to provide a guide for placement of subsequent devices into the vertebral body. A Jamshidi Needle is a long, tapered combination needle and drill that can be used for insertion into bone. An example Jamshidi needle and K-wire can be seen in FIG. 1A. Here, the Jamshidi needle 110 can include a tapered distal end 120 and a handle 130 at its proximal end. The elongate Jamshidi needle 110 can be hollow, to allow insertion of the K-wire 140 through the needle 140.

Figure 1B:
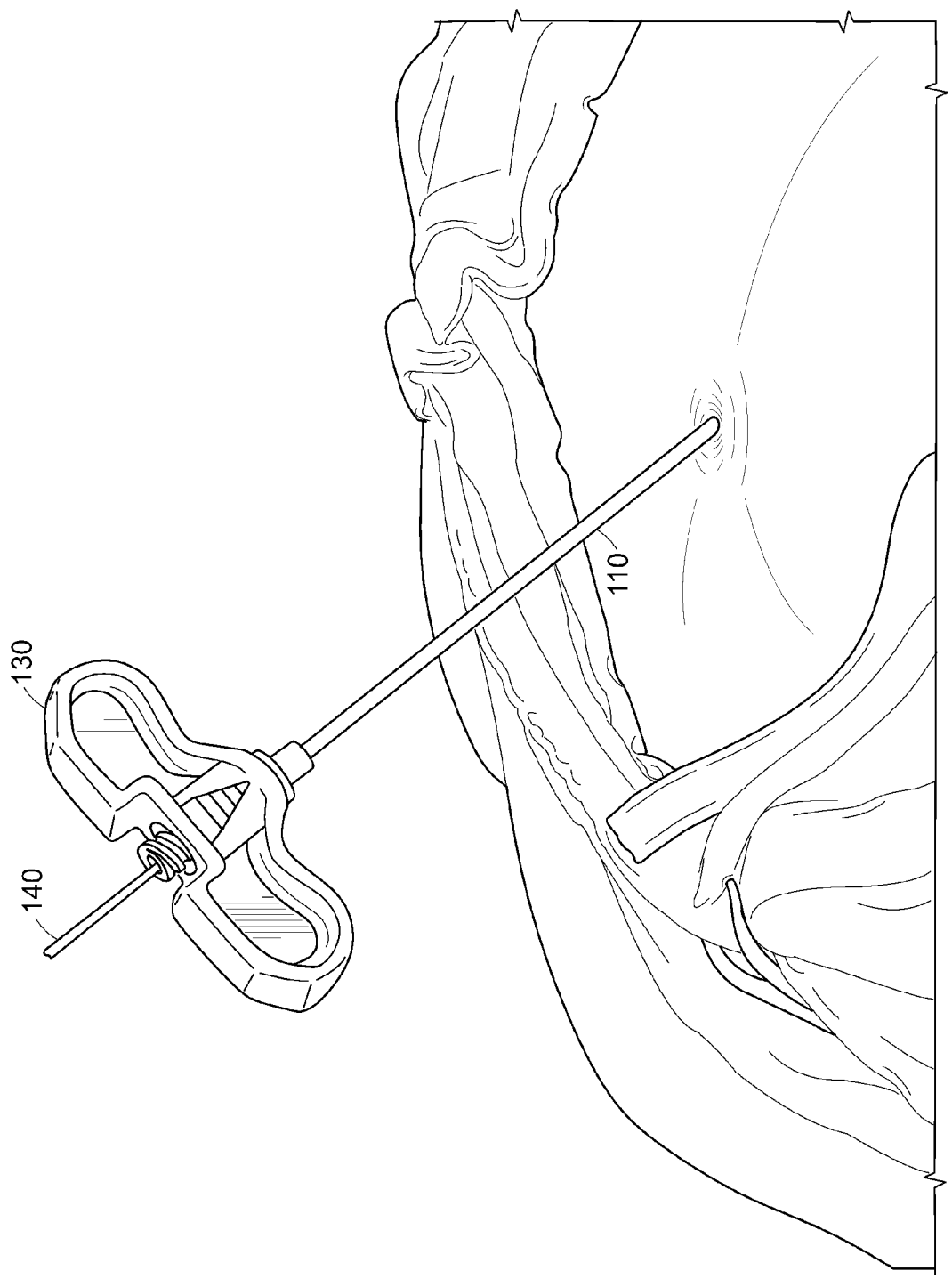
FIG. 1B is a picture of a Jamshidi needle being inserted into a patient, in accordance with one embodiment of the invention.

In operation, the tapered distal end 120 is inserted through the skin and underlying tissue and pressed against the outer wall of the vertebral body. The K-wire 140 can then be inserted through the hollow elongate needle 110 such that the distal end of the K-wire is forced against the wall of the vertebral body. The Jamshidi needle 110 and K-wire 140 can be forced into the wall of the vertebral body to any depth appropriate for the procedure. The Jamshidi needle 110 can then be removed, leaving the K-wire 140 in place to act as a guide needle for the placement of subsequent devices. An example of a Jamshidi needle 110 and K-wire 140 inserted through the skin and underlying tissue of a patient can be seen in FIG. 1B. In alternative embodiments, any appropriate needle type or other device may be used to provide initial access to the vertebral body.

Cannula & Trocar

In one embodiment of the invention, access to the vertebral body can be achieved through the use of a trocar and cannula assembly. This trocar and cannula assembly can be inserted over an already inserted guide wire or needle, such as the K-wire described above, or be inserted directly without the need for a guide wire.

Figure 2C:
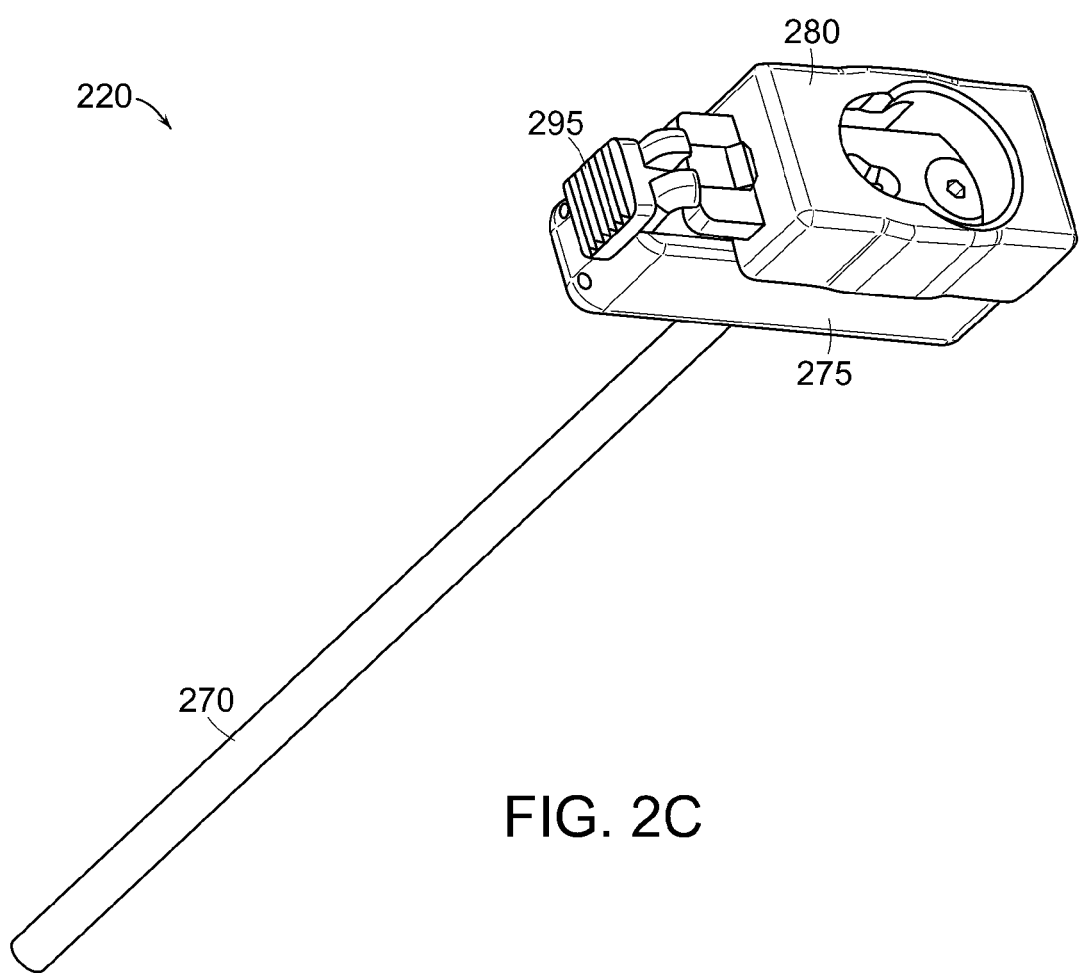
FIG. 2C is another schematic perspective view of the cannula of FIG. 2B.

One embodiment of a trocar and cannula assembly is shown in FIGS. 2A-2F. In this embodiment, the trocar and cannula assembly 200 can include a trocar 210 and a cannula 220. An example trocar 210 is shown in FIG. 2A. In this embodiment, the trocar 210 includes a hollow shaft 230 with a sharpened tip 240, and an impact handle 250 or knob coupled to the hollow shaft 230. The impact handle 250 also has a cylindrical locking flange 260, for releasable interlocking with the cannula 220. The trocar 210 can be configured to fit over a guide wire or needle.

An example cannula 220 is shown in FIGS. 2B and 2C. The hollow cannula 220 can include a thin walled straight tube 270 and a handle 275 with a locking feature 280 attached to the hollow tube 270. The locking feature can include a button, slide, latch, or other appropriate mechanism for releasable engagement with a flange. In the embodiment of FIGS. 2B and 2C, the locking feature 280 includes a locking slide 280 and a locking slide latch 295, wherein the locking slide latch 295 is configured to engage with the locking slide 280 and releasably hold the locking slide 280 in either a closed or open position. The thin walled tube 270 can also have a slot 285 along its axis on the proximal side that is continuous with a slot 290 in the handle 275. The tube slot 285 and the handle slot 290 can be used for instrument orientation or drills, reamers, etc. disposed in the cannula 220.

The handle 275 may be coupled to the thin walled straight tube 270 of the cannula 220 by any appropriate means, including, but not limited to, bonding, pressure fitting, threading, or any combination thereof. The handle 275 may be a plastic, metal, or any other suitable material. The handle 275 can include a locking feature for releasable retention of an instrument placed within the cannula 220. In one embodiment, the handle 275 can include a number of holes through its length, fitted with stainless steel rods, that may be used by the surgeon, under fluoroscopy, for circumferential orientation of the handle 275 and the cannula 220 to ensure the desired relationship between the cannula 220 and the vertebral body.

In one embodiment, the trocar 210 fits within the thin walled straight tube 270 of the cannula 220, and releasably locks to the locking feature 280 of the cannula 220 via the locking flange 260. When locked together, the sharp tip 240 of the trocar 210 can protrude beyond the end of the thin walled straight tube 270 of the cannula 220. In an alternative embodiment, the cannula may include a flexible hollow tube, or a curved hollow tube, allowing the cannula to be placed over a curved guide wire or other curved object.

In use, the trocar 210 and the cannula 220 may be deployed over a guide needle or wire and pressed into the vertebral body, with the trocar 210 providing the displacement and/or cutting means needed to force the cannula through the skin and underlying tissue of a patient and up against, and possibly through, the wall of a vertebral body. The guide wire may be a K-wire 140 as described above, or be any other appropriate needle, piercer, or guiding wire element. Once the cannula 220 is inserted through the outer wall of the vertebral body, the trocar 210 and guide needle can be removed, leaving the hollow cannula 220 in place as an access passageway for subsequent instruments and tools.

Figure 2D:
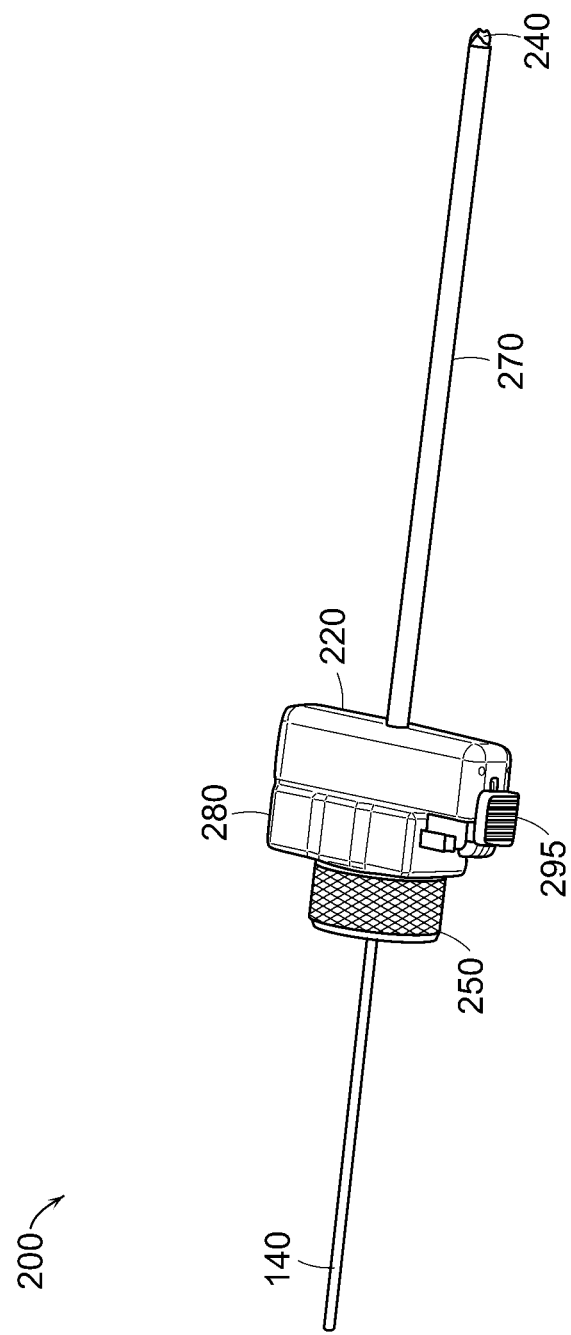
FIG. 2D is a schematic perspective view of a trocar inserted with the cannula of FIG. 2B, in accordance with one embodiment of the invention.

An example of a trocar 210 and guide wire 140 inserted through a cannula 220 can be seen in FIG. 2D. In FIG. 2D, the impact handle 250 of the trocar 210 is releasably coupled to the handle 275 of the cannula 220 by the locking feature 280. In one embodiment, the trocar tip 240 can protrude beyond the end of the thin walled straight tube 270 of the cannula 220 and can be rotated relative to the cannula tube 270, if desired. The entire trocar 210 and cannula 220 assembly is placed over the guidewire 140, that was previously inserted into the vertebral body. In one embodiment, a small mallet can be used to tap the trocar 210 to enlarge the hole until the cannula 220 is pressed into the vertebral body to a desired depth. The trocar 210 can then be unlatched from the handle 275 and withdrawn. At this point, the needle or guidewire 295 can also removed, leaving the cannula 220 in place and held immovably by the wall of the vertebral body.

Figure 2E:
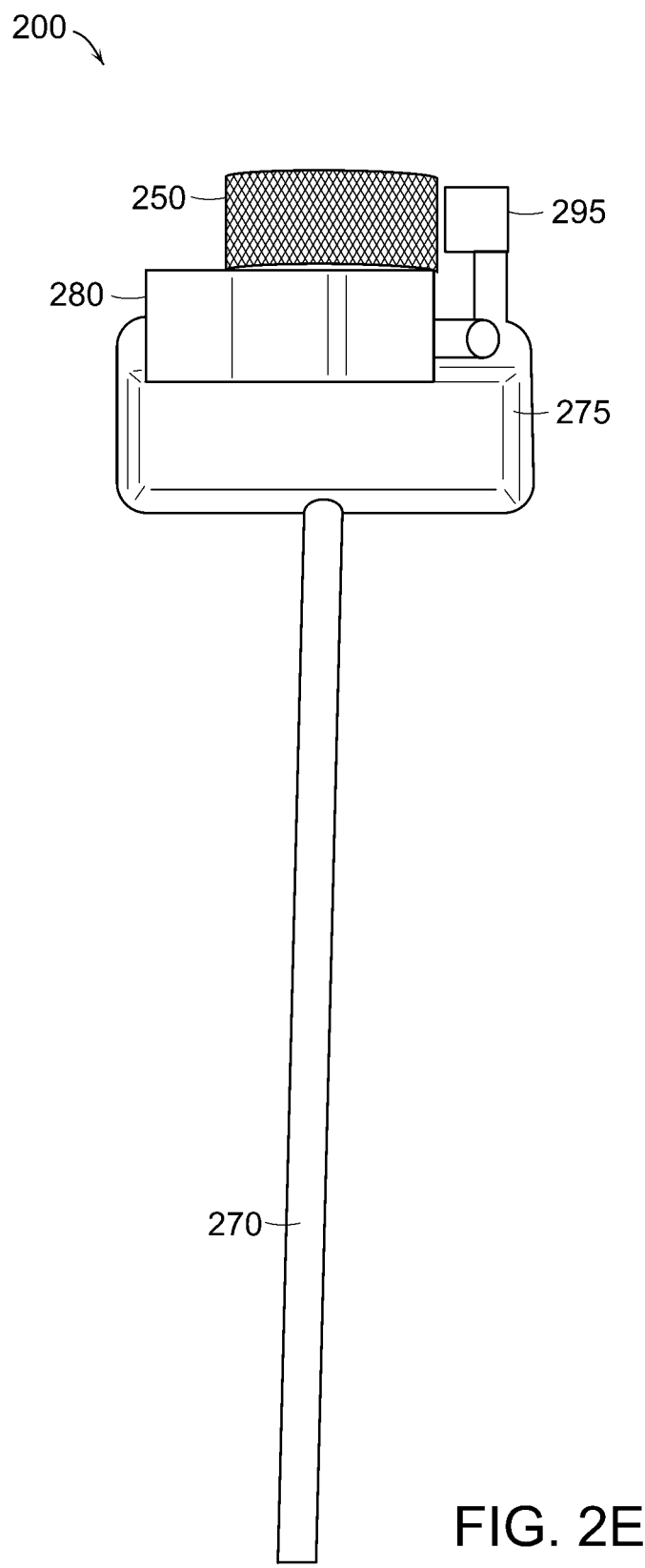
FIG. 2E is a schematic plan view of a cannula, in accordance with one embodiment of the invention.
Figure 2F:
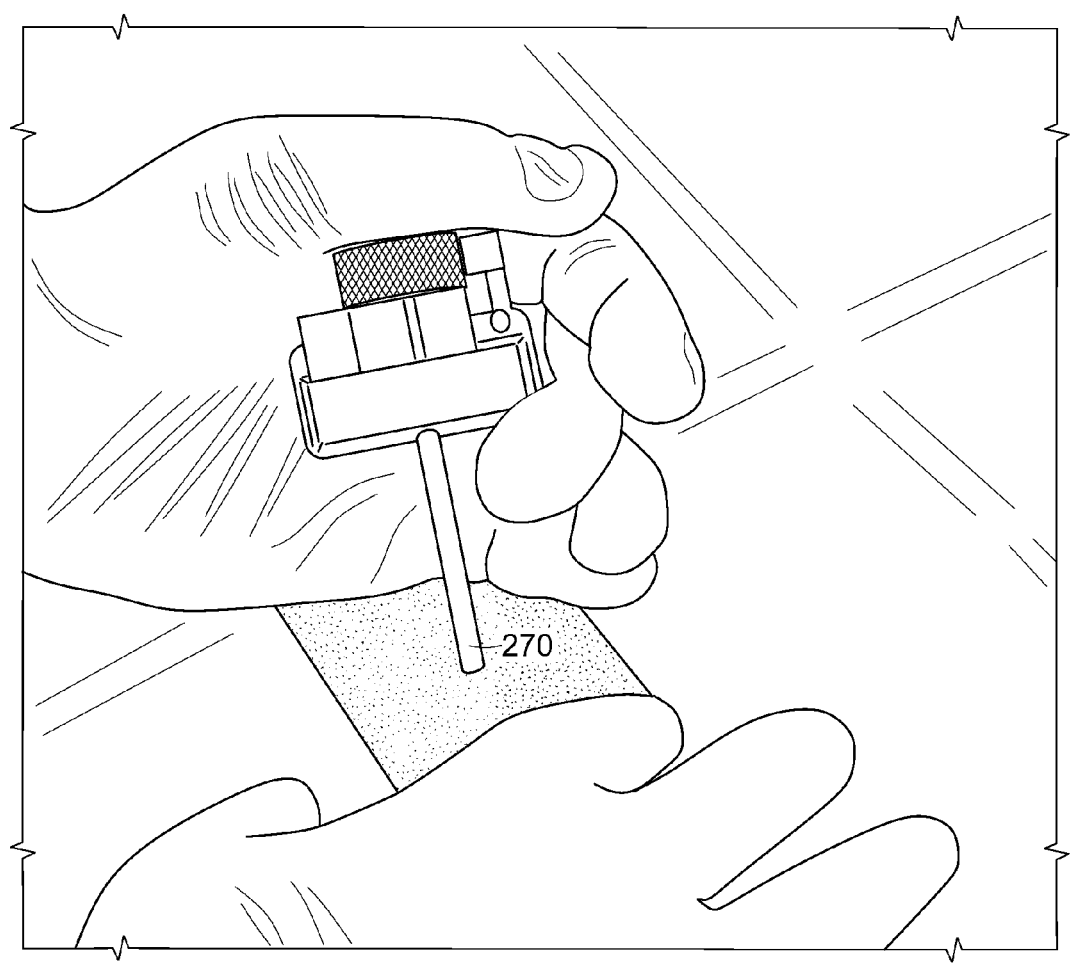
FIG. 2F is a picture of a trocar and cannula being inserted into a patient, in accordance with one embodiment of the invention.

An example embodiment of a cannula 220 and handle 275 can be seen in FIG. 2E. An example of this cannula 220 inserted into a patient can be seen in FIG. 2F.

Drill

In one embodiment of the invention, once the cannula is in place, the next step is to drill a curved hole in the vertebral body. The curved hole may be needed to make a cavity in the vertebral body that will go across the interior of the vertebral body so that medical cement will fill and support the entire vertebral body without the need to drill from both sides. One embodiment of the invention can include a means of providing a drilled curved path in the vertebral body through the use of a curved drilling device. Example curved drilling devices are shown in FIGS. 3A-3I.

Figure 3A:
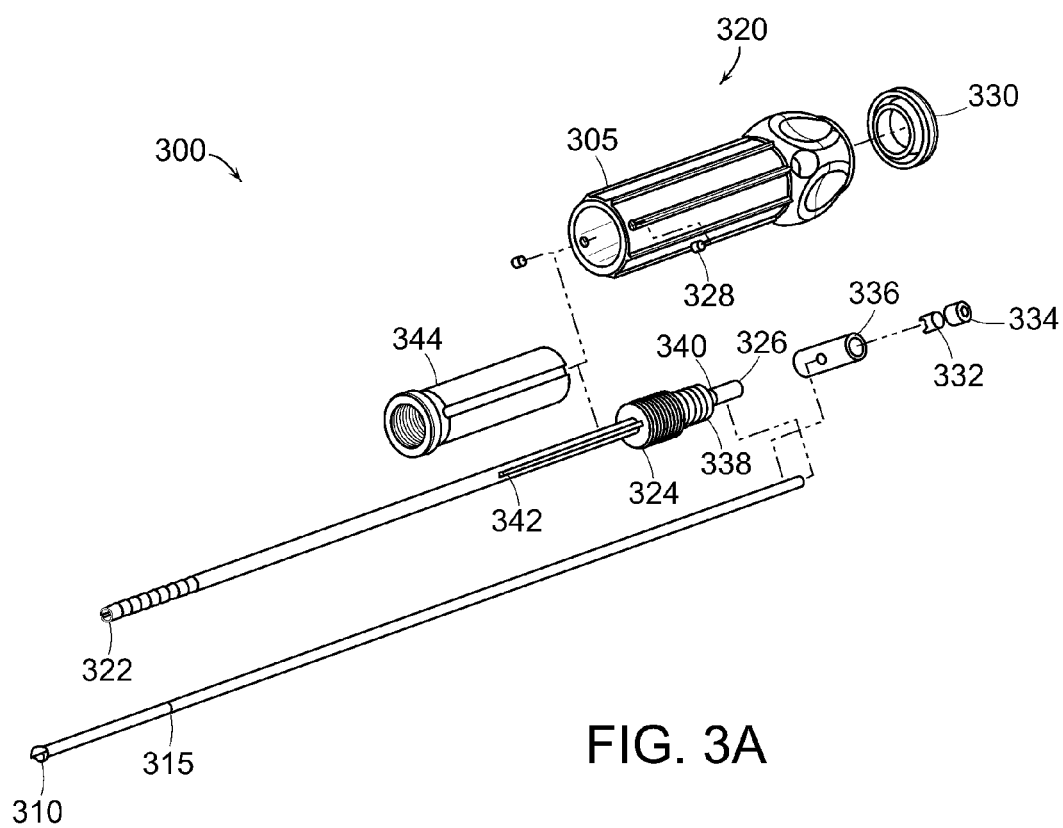
FIG. 3A is an exploded schematic perspective view of a drill assembly, in accordance with one embodiment of the invention.

In one embodiment of the invention, as shown in FIGS. 3A and 3B, the curved drill device 300 can include a drive handle 305, a sharp tip 310 attached to a flexible torque transmitting drive shaft 315, and a handle drive assembly 320. The flexible drive shaft 315 can be secured and contained by a spring loaded, flexible, slotted metal tube 322 having a feedscrew assembly 324 attached therewith. The proximal end of the drive shaft 315 can include a solid tube 326 bonded, or otherwise coupled, to the flexible shaft 315 component and having sufficient torque transmission capability to drive the shaft assembly. The rotating shaft/sharp tip 310 assembly can further be coupled to the handle assembly 320 by a cross pin 328, or other appropriate device, which can engage with a nut 344 located within the handle 305 and threaded onto the feedscrew assembly 324.

The handle drive assembly can include a number of components, including, but not limited to, a cap 330 for the handle, a clamp 332 for the torque tube, a locking element 334 for the torque tube, and a retainer element 336 for the torque tube. The retainer element 338 can be coupled to a spring element 340 to provide a spring force to a band or other element configured to provide a force to the distal portion of the flexible drive shaft 315 and slotted metal tube 322 to produce the correct curvature at the distal end of the drill 300.

One embodiment of the invention can include an inner tube sized to slide within the outer slotted tube. This inner tube can have an extensive laser cut opening along its distal portion. When assembled, the reduced cross section of this section of the inner tube lies adjacent to the slotted portion of the outer tube along the inside or concave side of the slotted tube. A compression spring of optimized stiffness can be coupled to the inner tube and the outer slotted tube at the proximal end by a lock washer, or other appropriate mechanism, that can be secured to a slot in the proximal end of the inner tube. When the washer is engaged, a tensile force is induced on the inner tube which causes the outer tube assembly to bend at the distal end. Upon bending, the slots on the medial side, which have been designed with gradually decreasing depth to encourage sequential distal to proximal deflection, can close. Therefore, when fully assembled under load of the spring, the outer slotted metal tube can assume a curved orientation with a desired radius of curvature. Since the slotted metal tube is itself flexible being made from hard temper stainless steel, or other appropriate material, it can be straightened against the force of the spring to pass through a straight cannula.

In one embodiment, the drive handle of the drill 300 can be a two part assembly featuring a grip feature suitable to allow manual rotation, coupled to a rotator component having locking flange. The locking flange can be designed to mate with the locking feature of a cannula handle to prevent axial movement but allow rotation. The rotator component can have a female thread throughout its length which can mate with a feedscrew slotted tube assembly. The feedscrew and a key are welded, or otherwise coupled, to the proximal end of the slotted tube.

When assembled to the hollow cannula, the key component 342 can slideably mate with the hollow cannula axial slot, which can rotationally lock the drill's curved slotted tube 322 in a preferred circumferential orientation. Therefore, when the handle assembly is rotated, the slotted tube advances in a fixed rotational orientation relative to the handle assembly at a pace equal to the thread pitch of the feedscrew. The rotating flexible drive shaft assembly, which is axially constrained within the slotted metal tube 322, also advances with the pitch of the feedscrew. The sharp rotating tip 310, by the combined forces of the feedscrew advance and internal spring force curving the shaft, cuts and advances on a curved helical path when the handle is rotated. Conversely, when the handle is counter rotated, the sharp tip retracts along the same curved helical path. If the lock engaging the curved drill is disassembled from the cannula, the device may be slideably removed from the cannula.

In operation, the distal end of the curved tube 322 of the drill can be slotted, perforated, composed of a different and or thinner material, or otherwise adapted to promote bending of the distal end. Any appropriate material, such as stainless steel, aluminum, or other metal, or a plastic or composite material may be used for the drilling device, as long as the material can provide sufficient strength, flexibility, resiliency, and resistance to fatigue. In one embodiment, different components of the drilling device can be constructed from different materials, including any of the materials described herein.

Figure 3E:
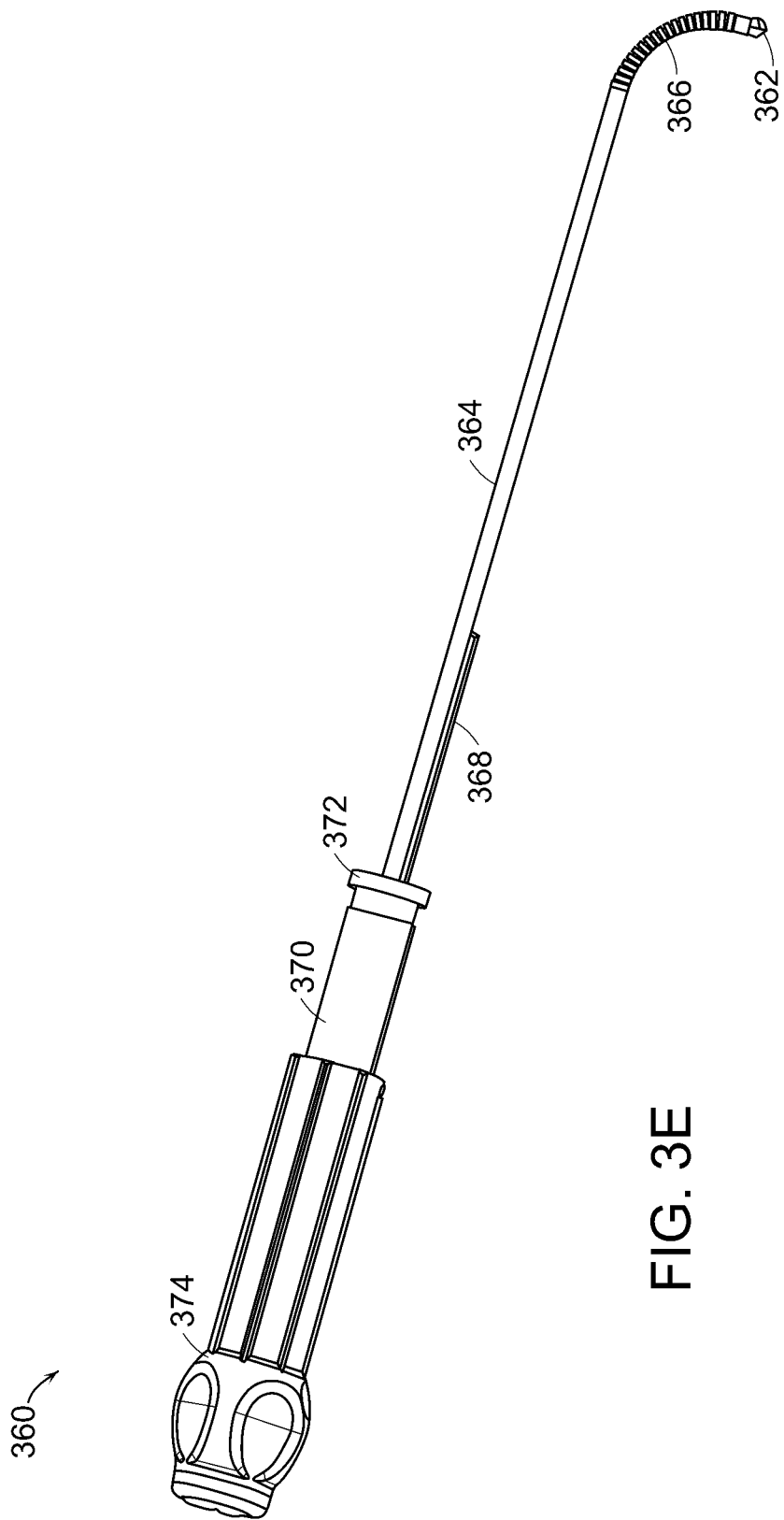
FIG. 3E is a schematic perspective view of another drill assembly, in accordance with one embodiment of the invention.

Another example of a curved drilling device is shown in FIGS. 3E-3I. As shown in FIG. 3E, the curved drilling device 360 can include a drill tip 362, a drill shaft 364 with a slotted portion 366 at the distal end for bending, an orientation key 368, a drill feed unit 370 complete with a locking flange 372 and a handle 374 for rotation.

The curved drilling device 360 releasably attached to a cannula and handle assembly 220 is shown in FIG. 3F. In one embodiment of the invention, when the curved drilling device 360 is initially installed into the cannula 376, the protrusion is only that of the drill tip beyond the cannula and as such, the slotted portion of the drill shaft is contained in the cannula and is therefore straight and not curved. The distal end of the drilling device 360 is free to curve once it has been deployed beyond the distal end of the cannula.

Figure 3H:
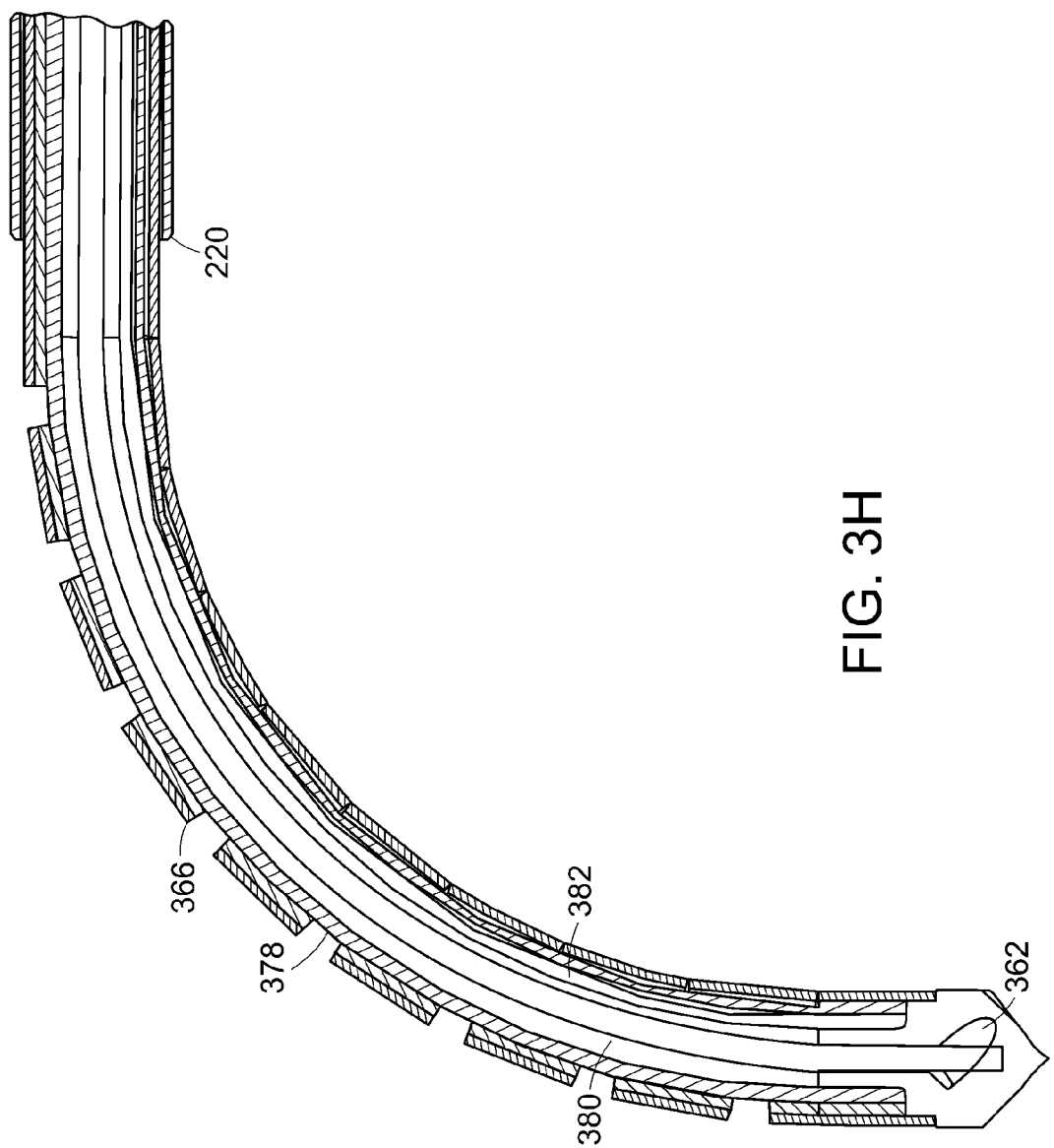
FIG. 3H is an enlarged sectional side view of the distal end of the drill assembly of FIG. 3E.
Figure 31:
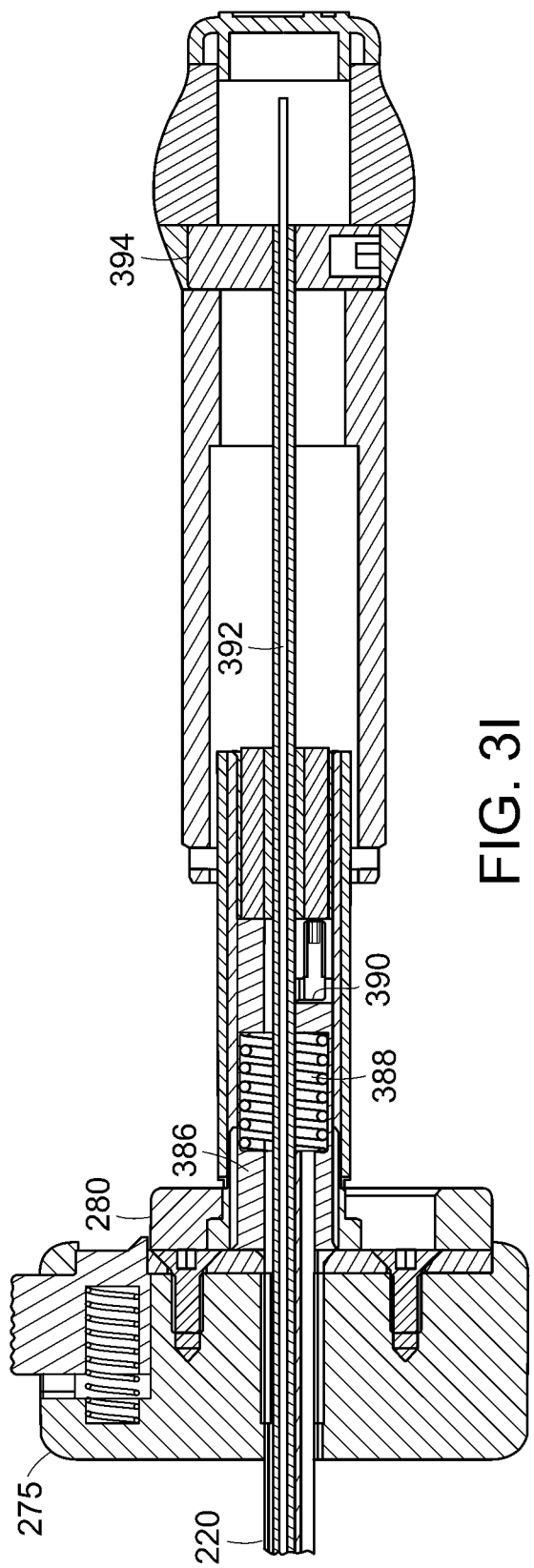
Figure 3J:
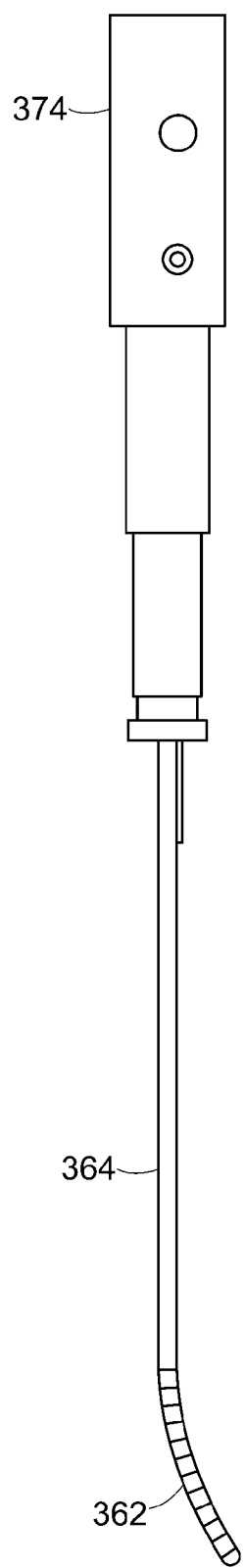
FIG. 3J is a schematic plan view of a drill assembly, in accordance with one embodiment of the invention.
Figure 3K:
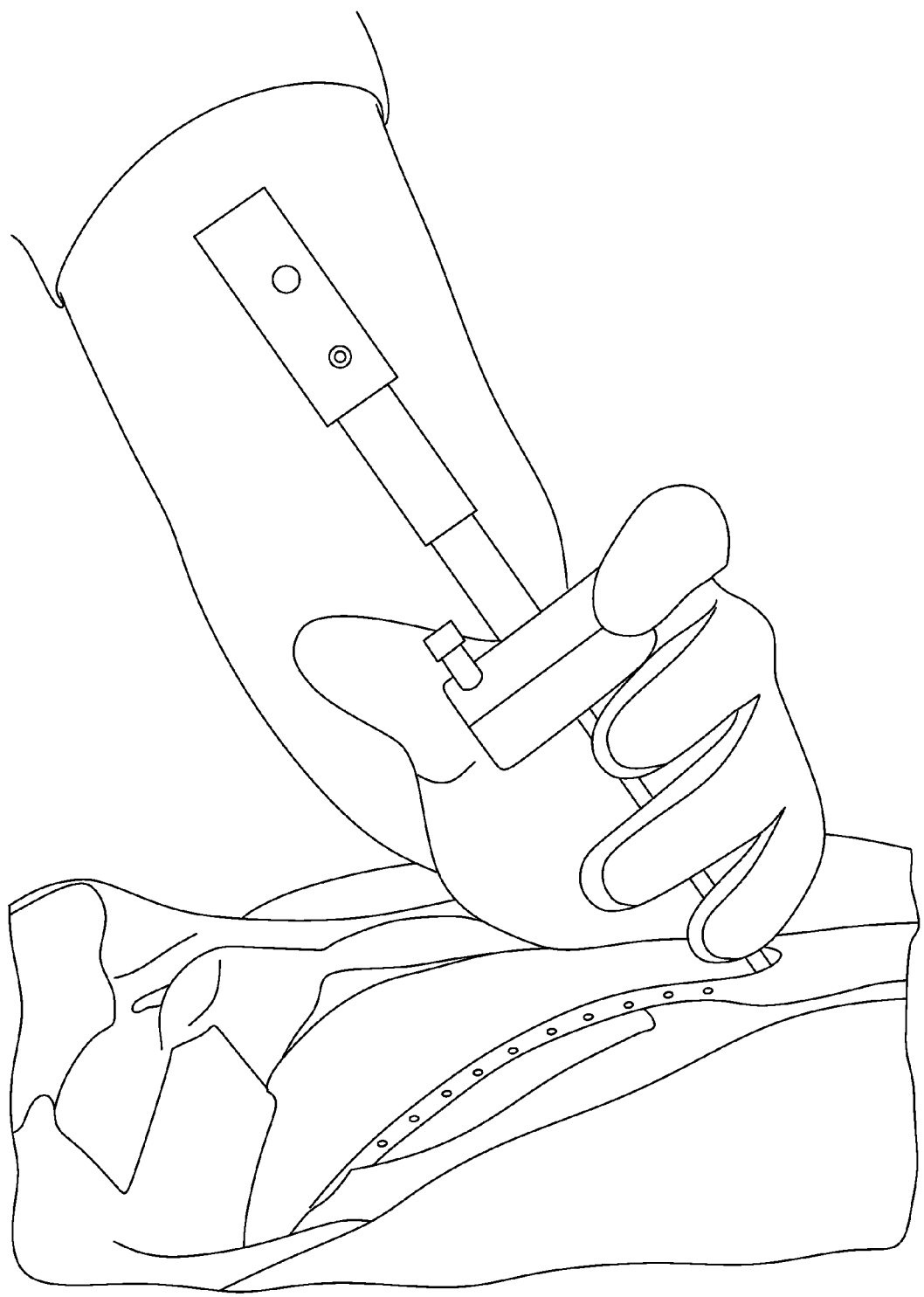
FIG. 3K is a picture of a drill assembly being inserted into a patient, in accordance with one embodiment of the invention.

A cross-section of the curved drilling device 360, depicting the internal mechanisms of the system, is shown in FIG. 3G. More detailed enlarged cross-sectional diagrams are provided in FIGS. 3H and 3I. In FIG. 3H the distal end of the drill unit is illustrated. In this embodiment, the drill tip 362 can be welded, bonded, threaded, or otherwise coupled, to a cabled torque tube 378 that provides rotation of the tip 362. The torque tube 378 may be an array of wires wound in a helical, circular manner that provides torque strength with the flexibility to "go around the corner" to deliver the necessary power to the drill tip 362 to cut bone. A drill safety cable 380 can be coupled to the drill tip 362 to promote drill tip retrieval in the unlikely event that it becomes detached from the cabled torque tube 378.

The slotted portion of the drill tube 366 is bent into a desired arc as it exits the cannula. This is achieved by means of the band 382, located on the inside of the bend and firmly attached to the drill shaft 364 at its distal end and attached to a compression spring assembly 384 at its proximal end. As a result, the band 382 can be held under spring tension, thus pulling on the inside of the drill shaft 364 to produce an arc, as desired.

FIG. 3I is a detailed cross section of the drill unit and handle, in accordance with one embodiment of the invention. In one embodiment, the locking flange on the drill unit can be retained by the locking flange of the handle. That, in turn, can be held in place by the locking slide 280 on the handle. The locking flange component can also have an internal thread or drill feed nut.

In one embodiment of the invention, a feed screw 386 includes a matching male thread. The proximal end of the drill shaft can be affixed to the feed screw 386 by welding, bonding, threading, or other means, and the feed screw 386 and drill shaft can have a key, also attached by welding or other means, to ensure the desired circumferential orientation of the drill shaft within the cannula 220. The key interface can align the handle plane to the plane of the curved drill shaft. One embodiment can also include a compression spring 388 for providing a pulling force on the band in order to bend the distal end of the drill shaft to the desired arc. A band retention device 390 can contain the compression spring 388. The compression can be preloaded to a desired force and the band retained to ensure that there is always tension on the band. In one embodiment of the invention, the spring 388 may be compressed as the band is pulled distally to allow for straightening of the drill shaft when passing through the cannula.

In one embodiment, the torque tube 392 can go through the drill shaft and feed screw, as well as through the band retention device, and be fastened to the handle 374 by the torque retention device 394 that is keyed to the rotation handle 374. The drill safety cable can go through the entire length of the torque tube and the excess can be tied into a knot. Alternatively, a ferrule can be staked to the drill safety cable so that it does not slide out of the torque tube inadvertently.

In operation, according to one embodiment of the invention, as the handle 374 is rotated the pins in the handle interact with the slots in the drill feed unit and cause it to rotate. This action causes the feed screw to move and advance the drill while rotating the drill tip 362 for cutting. This motion allows the drill tip 362 to cut a curvilinear path through the interior of the vertebral body. The progress of the pathway can be monitored by use of a medical imaging technique, or be measured by means of a distance scale associated with the drill and indicating the extension of the drill tip beyond the end of the cannula.

An example embodiment of a drill assembly can be seen in FIG. 3H. An example of this drill assembly inserted into a patient can be seen in FIG. 3I.

Reamer

In one embodiment of the invention, the curved path created by the drill device can be enlarged by a reamer device. Enlarging the cavity can allow it to accommodate the stent and that medical cement that will ultimately be injected into the cavity. An example of a reamer device is shown in FIGS. 4A-4G.

In one embodiment, the distal end of the reamer is configured for insertion through a cannula into a vertebral body. The reamer can include an orientation key configured to mate with a corresponding slot in the cannula to ensure that the distal end of the reamer is deployed at the correct circumferential angular orientation. The reamer may be releasably lockable in the cannula.

In one embodiment, the reamer can include a circumferentially partially slotted outer tube, wherein the slots enable the distal end of the reamer to bend in a predetermined direction. The reamer may include a band inserted within the outer slotted tube and coupled to the distal and the proximal ends of the reamer to bend the slotted outer tube in a predetermined direction and at a set angle. The proximal end of the band may be coupled to a compression spring to provide a predetermined amount of flex to the distal end of the reamer, thus allowing the distal end to be straightened while being inserted through the cannula, and then return to its predetermined bent configuration upon being extended beyond the end of the cannula.

The reamer may include a reamer blade yoke configured to extend from the distal end of the outer slotted tube. A reamer blade may be pivotably coupled to the reamer blade yoke by a pivot pin. The reamer may include a cabled torque tube coupled to the reamer blade yoke to rotate the reamer blade yoke and coupled reamer blade while the outer slotted tube remains stationary. A cable may be extended through the cabled torque tube and coupled to the reamer blade to provide a force to pivot the blade about the pivot point from a neutral, centered configuration to a tilted/opened configuration. The cable may be attached, at the proximal end of the reamer, to a compression spring. The compression spring attached to the cable can eliminate slack in the cable and allow the angle of the reamer blade to elastically deflect from its set angle.

In one embodiment, the proximal end of the reamer may include a handle. The handle may include a blade opening sleeve. Rotation of the blade opening sleeve can open or close the reamer blade with or without rotating the blade. The handle may also include a rotation handle. Rotation of the rotation handle can rotate the reamer blade about the reamer blade yoke. Rotation of the rotation handle can also provide a proximal movement of the distal end of the reamer back towards the distal end of the cannula;

In operation, in one embodiment of the invention, rotation of the reamer blade, while opening the blade, results in a semi-spherical cavity being created. Once the blade is fully opened, rotation of the rotation handle provides a rotational movement and a proximal movement of the reamer blade, allowing the reamer blade to follow a generally helical path to create a curved, generally cylindrical cavity of a length determined by the amount of rotation of the rotation handle. The proximal end of the reamer may include markings to indicate the amount of proximal movement of the distal end of the reamer from an original, fully extended position. Rotation of the blade opening sleeve in the opposite direction can return the reamer blade to a neutral/centered orientation. Upon returning the reamer blade to the neutral/centered orientation, the reamer may be unlocked and removed from the cannula.

In one embodiment, the reamer device may be similar in construction to the drill devices described above. Both devices can have a slotted tube assembly and a flexible torque transmitting drive shaft contained therein. Both devices can have an internal tube welded, bonded, or otherwise coupled at the distal end, and joined by a washer and compression spring at the proximal end. However, the reamer device can have a moveable blade disposed at its tip. The moveable blade can be attached to a yoke by a pivot pin, and to a cable tether that is crimped, bonded, welded, or otherwise attached to the moveable blade at a location distal to the pivot pin.

More specifically, a reamer device 400 for enlarging the drilled cavity to a desired diameter and curvilinear length is shown in FIG. 4A. The reamer device 400 may have similarities to the drilling device described above in that it has a shaft 405 that is slotted at the distal end 410 for curving, and the curving is produced by a band that is spring loaded by a compression spring situated between the feed screw and the band retention device. In this embodiment, the reamer device 400 includes a reamer blade 415 that is pivotably coupled to a yoke 420 that is mounted on the distal end of the shaft 405. An orientation key 425 may be mounted to the shaft 405 to engage with a slot in a cannula and ensure the correct circumferential orientation of the reamer device upon insertion. At its proximal end, the reamer device 400 can include a dual function handle 428 including rotation handle 430 for rotating the blade 415, a blade opening sleeve 435 for deploying the blade, and a reamer feed nut 440 for moving the blade back and forward along the axis of the shaft as the blade is rotated. The proximal end of the handle 430 may be a tubular molded component with gripping features on its external surface. In an alternative embodiment, the handle 430 may be manufactured from any appropriate metal, plastic, ceramic, composite material, or combination thereof. Rubber or fabric elements may also be placed on the outer surface of the handle 430 to promote grip.

Figure 4E:
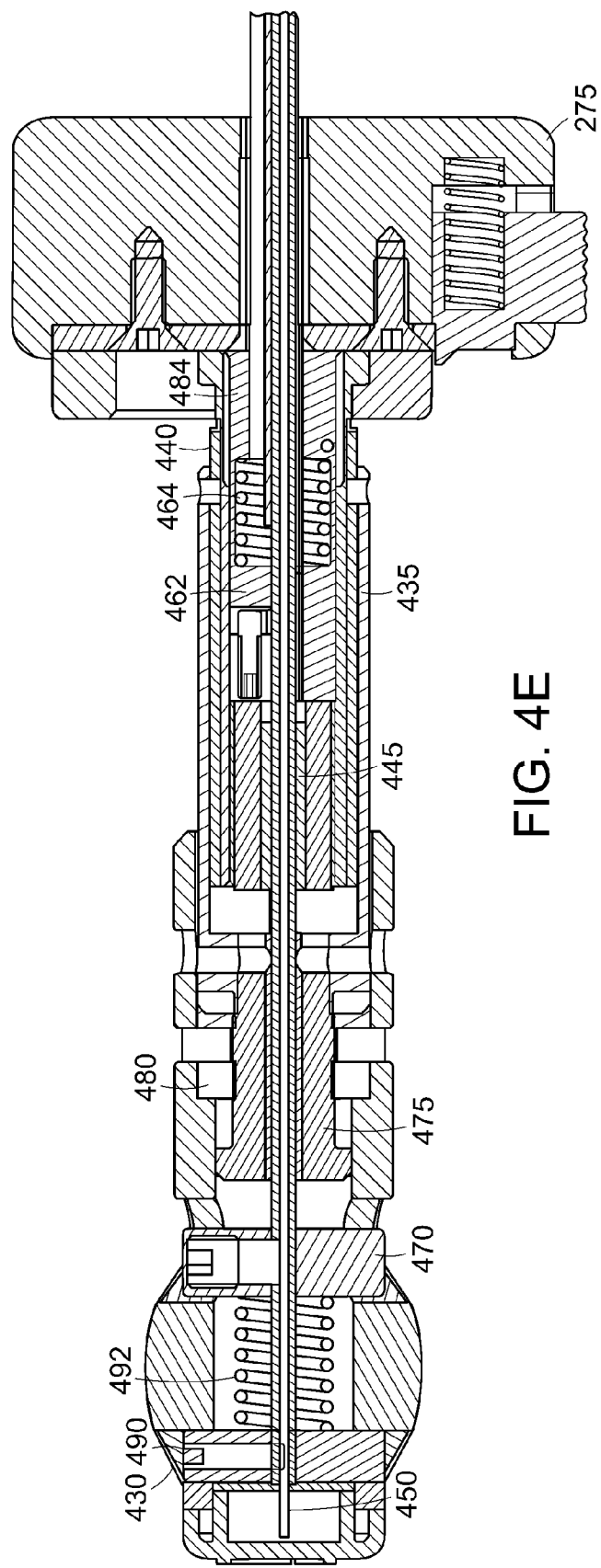
FIG. 4E is an enlarged sectional side view of the proximal end of the reamer assembly of FIG. 4A inserted within a cannula.

The reamer device 400 releasably attached to a cannula and handle assembly 220 is shown in FIG. 4B. A cross section of the reamer device 400, depicting the internal mechanisms of the system, is shown in FIG. 4C. More detailed cross-sectional diagrams are provided in FIGS. 4D and 4E.

In one embodiment, the reamer assembly may also be retained in the cannula and handle assembly 220 in the same manner as described above for the drilling device. The reamer feed nut 440 may work in the same way as described above for the drilling device feed nut. In one embodiment, a torque tube 445 can provide power for reaming (enlarging) the drilled hole, with the torque tube 445 driving the yoke 420 that houses the pivoting reamer blade 415. An inner cable 450 that goes through the center of the torque tube 445 can be used to tilt or open the blade 415 from the neutral position aligned with the axis of the shaft 405 to a deployed position at an angle to the axis of the shaft 405. The blade 415 can tilt or pivot about a pivot pin 455 coupled to the reamer blade yoke 420. As with the drilling device above, the curvature of the distal end of the reamer device 400 can be set by a band 460 placed within the slotted tube 410 and held in tension by a spring element at the proximal end of the reamer device 400. The fully deployed angle may be set at any appropriate angle. In one embodiment, the deployment angle may be set at any angle up to 90°. For example, the fully deployed angle may be in a range from 20° to 90°, or from 30° to 70°, or from 45° to 60°.

The curvature of the distal end may be set to any appropriate angle by correct selection of the band length. A band retention device 462 can hold the band 460 at the proximal end of the reamer device 400, with a compression spring 464 coupled to the band retention device 462 to allow the shaft 405 to flex from its preferred steady state curvature during deployment through the cannula 220 and upon contact with a "hard" element within the vertebral body.

The reamer device 400 can include a multi-component, dual function handle. A cross-section of an example handle is shown in FIG. 4E. In one embodiment of the invention, a lost feed motion may be needed to open the reamer blade, while rotating the reamer handle, with the feed system remaining still. This feature is provided by means of a blade opening sleeve 435. In one embodiment, this may be achieved by a rotation of the handle to initially "telescope" the handle from the blade opening sleeve 435 to pull on the center cable 450 to open the reamer blade 415 all while no feeding motion occurs. A torque tube retention device 470 travels in an elongated slot in the rotation handle 430 so no proximal movement results. The blade opening sleeve 435 retains a "T" screw 475 that provides the proximal movement of the handle for blade opening and when a blade opening nut 480 stops on the head of the T screw 475, rotation is now transferred to the reamer feed nut 440.

The reamer feed nut 440 rotation pulls the feed screw 484 proximally and at the distal end the reamer blade is rotating and feeding proximally resulting in cutting bone and creating a curved cavity to desired length with fluoroscopy, or other appropriate means, for visual reference. After the desired length of cavity has been achieved, the rotating handle 430 is rotated counter to the cutting direction and the reamer blade 415 will fold back inward to the center starting position. The reamer assembly can be unlatched from the handle and removed. The cannula and handle assembly 220 can remain in place, however, so that further devices, such as devices that permit the insertion of the stent and the medical cement, can be inserted into the enlarged cavity.

The cable 450 originating from the moveable blade may be fed through the entire assembled device and terminated and crimped, or otherwise coupled, to a cable retainer 490, such as a cross pin assembly, that is coupled to the wall of the rotation handle 430. A spring 492 may be located within the proximal inner border of the rotation handle 430 adjacent to the cable retainer 490. A thread may by used to couple the rotation handle 430 to the remainder of the reamer device 400.

In one embodiment, the dual function handle 428 may induce a tensile force on the cable tether 450 by rotating the proximal molded component relative to the distal handle component to effectively lengthen the handle. The cable tether thereby pulls the moveable blade 415 to cause a pivoting of the blade from a closed to an open position. The handle 428 can then cause the rotation of the flexible drive shaft assembly to rotate the blade 415 within the cavity.

The handle assembly, including the distal and proximal components, may be further secured to a rotator component having an internal thread mating the feedscrew component 484 of the slotted tube assembly. Thus, its function may be substantially identical to that of the drilling device described above. However, the feedscrew rotation may not be enabled until the reamer blade has been fully deployed via rotation of the proximal component of the handle 428. Therefore, in one embodiment, when the rotation handle 430 is rotated, the moveable blade assembly first rotates and deploys, then translates due to the action of the feedscrew mechanism 484. The deployed blade therefore enlarges the path to a required diameter by simultaneously rotating and translating the blade 415. The direction of translation, in one embodiment, is retrograde, which is achieved by the use of a left hand thread in the feedscrew 484.

In one embodiment, the blade deployment from a neutral to an open position may only occur when the blade is rotating. In an alternative embodiment, the blade deployment may be independent of the blade rotation. The rate of blade deployment from a closed to an open position is dependent on the pitch of the thread which joins the proximal and distal handle component.

In an alternative embodiment, the reamer device may be configured to drill into the vertebral body as it is advanced, before being deployed to extend the size of the cavity, as described above. In this embodiment, the reamer device can function as both a reamer and a drill, thus eliminating the need for a separate drilling device.

Figure 4F:
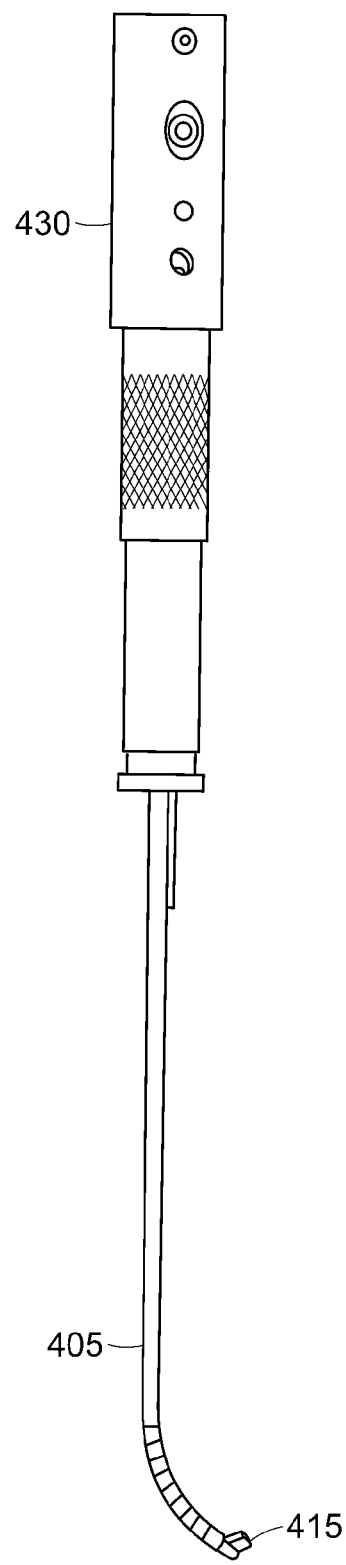
FIG. 4F is a schematic plan view of a reamer assembly, in accordance with one embodiment of the invention.
Figure 4G:
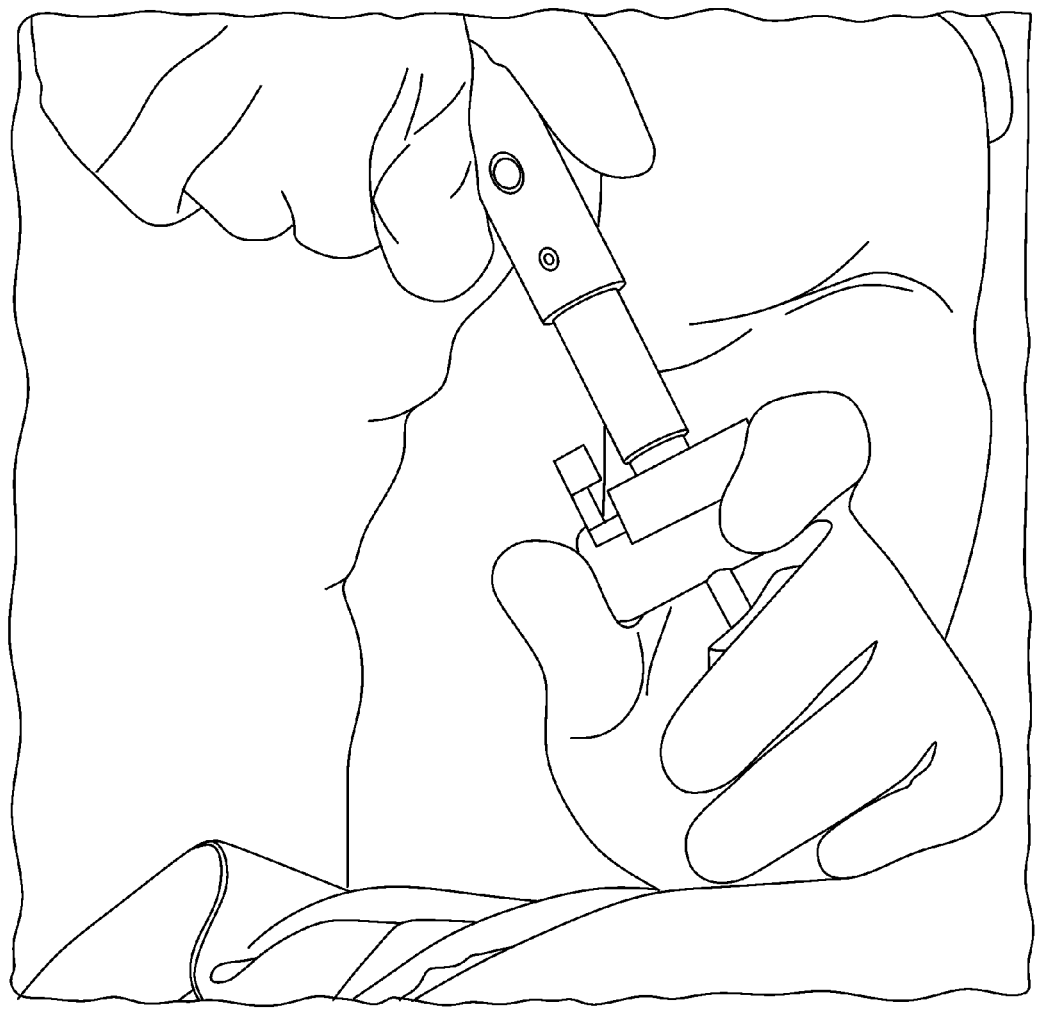
FIG. 4G is a picture of a reamer assembly being inserted into a patient, in accordance with one embodiment of the invention.

An example embodiment of a reamer device can be seen in FIG. 4F. An example of this drill assembly inserted into a patient can be seen in FIG. 4G.

Method of Use

The devices discussed herein may be used in conjunction to provide a method of creating a curvilinear cavity within a vertebral body, or other bony structure. As disclosed herein, the creation of a curvilinear pathway and cavity within a vertebral body allows the cavity to extend over a potentially larger region of the interior of a vertebral body, and bisect an axis of the vertebral body using only a single point of access. After creation of a cavity in a damaged or diseased vertebral body, the cavity can be filled with a medical cement or other treatment element to stabilize the vertebral body and alleviate pain. As a result, the creation of a curvilinear pathway and cavity using these devices can enable the complete stabilization of a vertebral body from a single access incision, thus reducing the time needed for a surgical procedure and the damage caused to surrounding tissue and bone during a procedure. This can greatly improve the efficiency and safety of such a procedure.

In one embodiment of the invention, a procedure for using the devices disclosed herein can be used to produce a curvilinear cavity within a vertebral body. One example embodiment of the invention further includes a method of placing a stent within a vertebral body. The stent can be a self-expanding, covered stent that allows interdigitation and prevents leakage of bone cement in undesired directions. In one embodiment, a single stent can be placed at a mid-line location of a vertebral body, rather than placing multiple stents on either side of the mid-line, thus reducing the time and fluoroscopy exposure require during a surgical implantation procedure.

In one embodiment, the method of creating a cavity for within a vertebral body, or other bony body, can include first creating a posterior pathway to the vertebral body, using a extrapedicular or intrapedicular approach, with a Jamshidi needle and/or K-wire. This may be performed, for example, using a dual C-arm technique to place and medialize the Jamshidi needle/K-wire to the fullest extent.

A working channel and trocar assembly can then be inserted along the pathway created by the Jamshidi needle/K-wire. This can be performed, for example, by locking the trocar into the working channel, inserting the working channel into the pathway, and tapping the assembly into place until the distal tip of the trocar and working channel extends, in one embodiment, 1-3 mm beyond the posterior wall of the vertebral body. The trocar can then be removed, leaving the open working channel in place.

A curved pathway through the vertebral body can then be created using a curved drill. This may be achieved using any of the drill arrangements described herein. In one embodiment, the drill depth markings at the user interface are set to "0" mm prior to insertion into the working channel. The drill can then be locked into the working channel with the key facing in the medial direction, thus ensuring the correct direction of curvature of the drill within the vertebral body. The handle of the drill can then be rotated to advance the drill tip into the vertebral body, with fluoroscopy, or some other appropriate technique, used to determine when the desired depth of penetration is achieved. The drill can then be removed and the depth markings on the user interface recorded. In one embodiment, the drill tip is oriented in the contralateral anterior quadrant of the vertebral body, thus assuring proper cavity positioning and bilateral cement filling.

In one embodiment, a larger cavity can then be created within the vertebral body by reaming out the hole created by the curved drill with a curved reamer. This may be achieved, for example, by first setting the depth markings on the user interface of the reamer to match those recorded for the drill depth, thus assuring that the reamer is positioned correctly within the vertebral body. The reamer can then be advanced fully into the pathway created by the drill and locked into the working channel, with the position of the reamer confirmed using fluoroscopy or some other appropriate technique. The blade of the reamer can then be opened, for example by rotating a portion of the handle of the reamer, and reaming can be carried out by rotating the handle. In one embodiment, the reamer may be stopped approximately 1-3 mm before approaching the distal tip of the working channel, with the position confirmed by fluoroscopy, or some other appropriate technique. The blade can then be closed (for example by rotating a portion of the handle in the opposite direction), and the reamer removed. In one embodiment, due to blade deflection, the cavity created by the reamer can have a slight taper from the distal end to the proximal end.

Once a cavity has been created, a stent delivery system can be locked into the working channel to correctly position a stent within the vertebral body. Once the stent has been positioned, a sheath covering the stent can be removed to deploy and expand the stent, and cement can be injected into the stent by attaching a syringe to the proximal end of the delivery system. The desired amount of cement can be injected into the stent with fluoroscopy, or some other appropriate technique, being used to monitor the flow of cement into the stent. Once the requisite amount of cement has been injected, the stent can be released from the delivery system and the delivery system removed from the working channel, thus leaving the stent in place within the vertebral body. The working channel can then be removed and the access pathway sutured or otherwise closed.

Figure 5A:
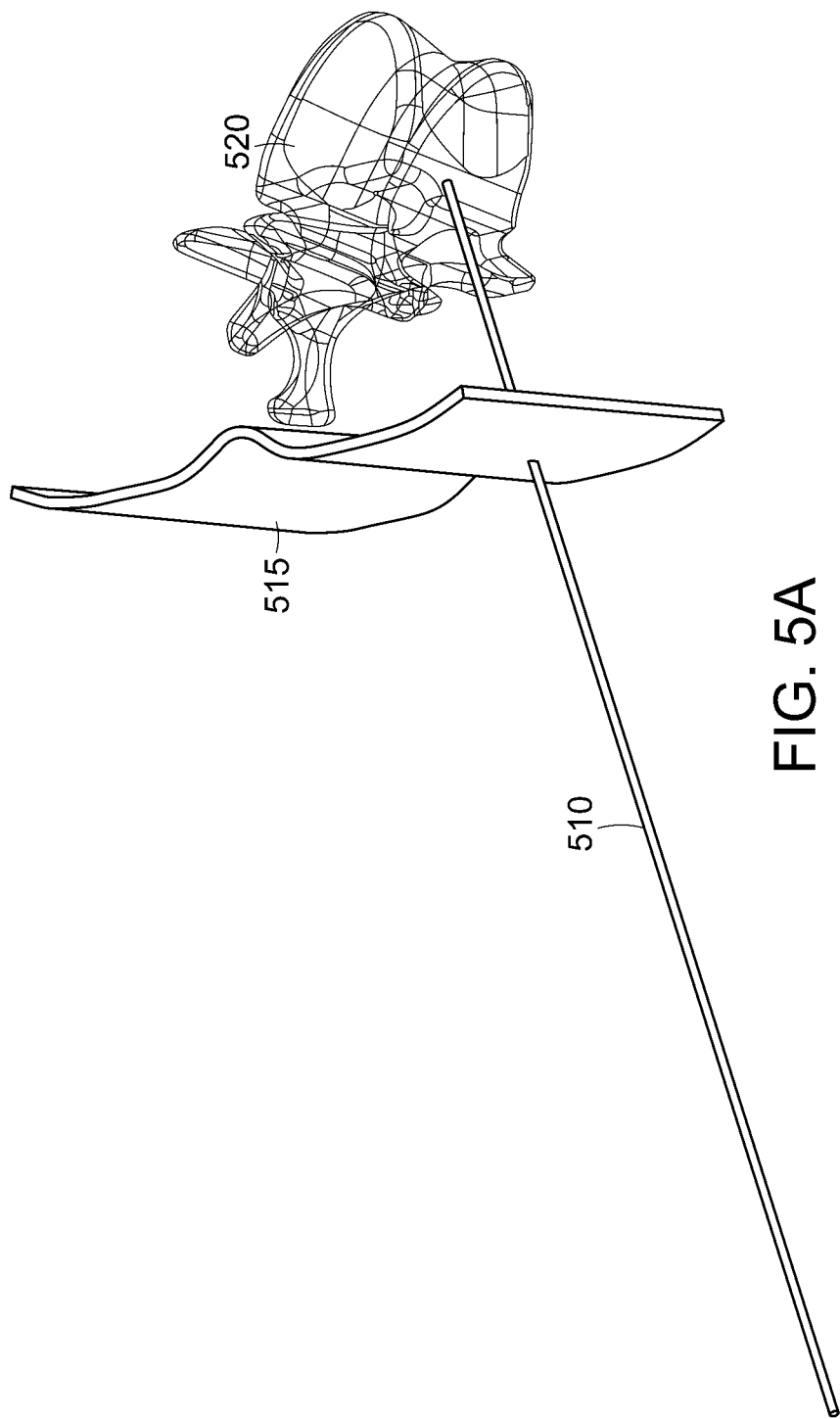
FIG. 5A is a schematic perspective view of a needle being inserted into a vertebral body, in accordance with one embodiment of the invention.

In one example embodiment, the pedicle of the vertebral body is first located. A needle assembly is then inserted percutaneously from the posterior approach through the outer tissue and anchored into the bone of the vertebral body to a suitable depth. This needle or wire will provide a guide for subsequent instruments. In one embodiment, the needle is a 1.5 mm diameter stainless steel pointed wire, although in other embodiments any appropriate diameter and material of needle may be used. The needle may be solid or hollow, depending upon the specific requirements of the procedure. An example of a guide wire or piercer 510 being inserted through the outer tissue 515 of a patient and into a vertebral body 520 by a posterior approach can be seen in FIG. 5A.

Once the guide wire 510 is in place, a trocar can be inserted into, and releasably coupled to a cannula, and the resulting trocar and cannula assembly slid over the guide wire 510. The trocar impact knob can be tapped with a hammer or other instrument to force the trocar forward to enlarge the hole in the vertebral body and thereby force the tip of the trocar and cannula into the bone. Once the trocar and cannula assembly have been correctly positioned, the trocar and the guide wire can be removed, thus leaving the cannula in place on its own. This cannula can then serve as a delivery path into the vertebral body for subsequent instruments.

Figure 5B:
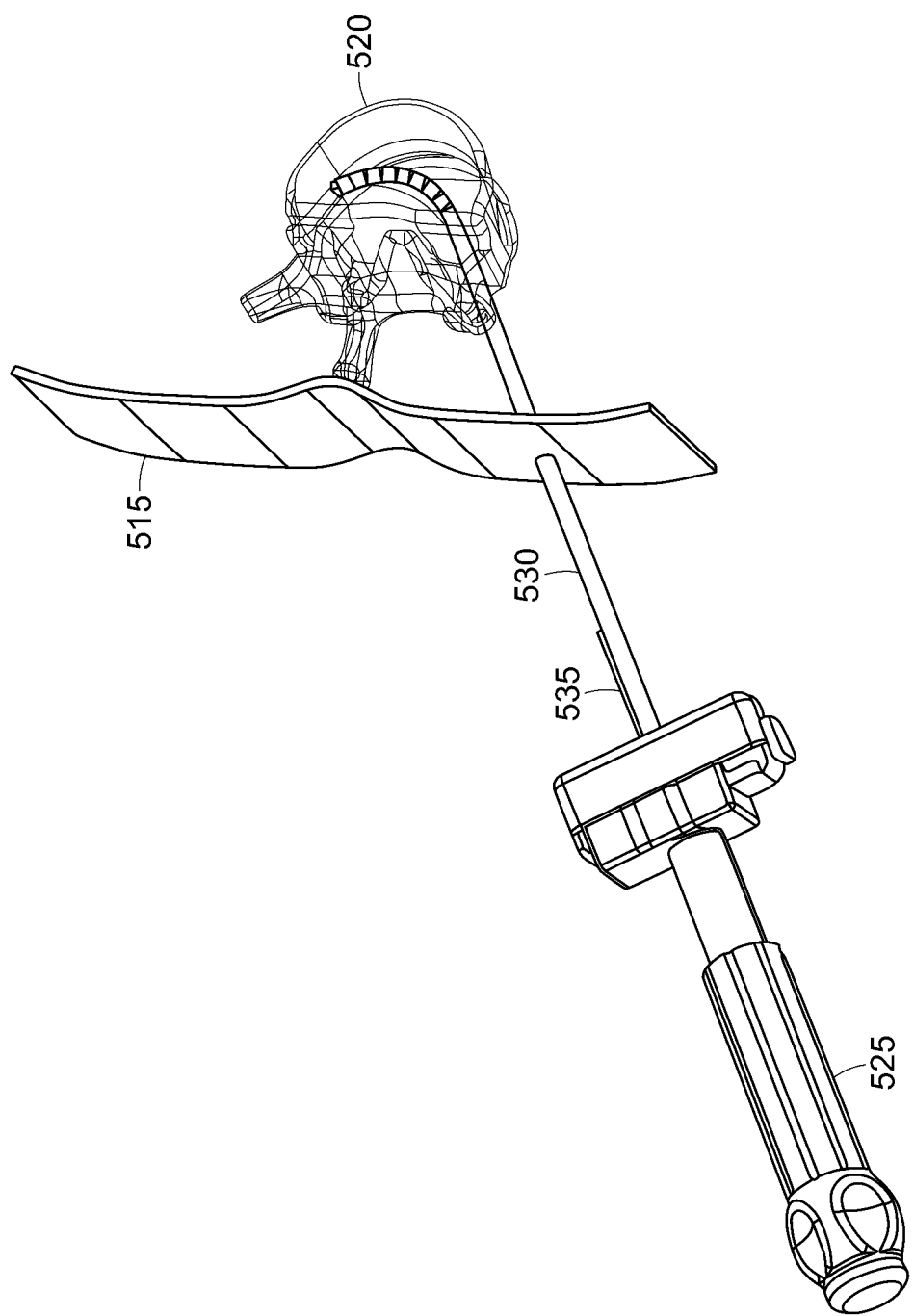
FIG. 5B is a schematic perspective view of a drill assembly being inserted through a cannula into a vertebral body, in accordance with one embodiment of the invention.

A curved drilling device can then be inserted through the cannula to create a curvilinear pathway through the vertebral body. An example of a drilling device 525 being inserted through a cannula 530 and into a vertebral body 520 can be seen in FIG. 5B.

The drilling device 525 can be slideably placed within the cannula by aligning the key on the drill 535 with the slot on the cannula. The drilling device 525 can then be fully inserted and releasably locked to the cannula 530 by sliding a locking tab to the lock position, or otherwise securing the drilling device 525 to the cannula 530. In this position, the curved slotted tube of the drilling device 525 is constrained in the straight tube of the cannula 530 and the sharp drill tip is positioned at the end of the cannula 530. After the drilling device 525 is secured to the cannula 530, for example by the locking the flange to the cannula handle, the drive handle of the curved drill can be rotated to cause the rotation of the flexible drive shaft assembly and sharp tip. Rotation of the flexible drive shaft assembly and sharp tip can also cause the simultaneous translation of the slotted tube and feedscrew assembly relative to the drive handle and cannula 530, thus translating the tip of the drilling device 525 into the vertebral body along a curvilinear path, provided the handle is locked to the cannula. For example, as it is being fed forward, the distal end of the drill shaft will begin to protrude from the cannula and starts to curve in the desired direction as it is cutting. The farther the drill shaft exits from the cannula, the greater the curved protrusion. As the drill tip rotates and travels in an arc, the resultant hole that it creates is also in an arc until the desired depth is achieved.

The sharp tip advances within the bone according to the pitch of the feedscrew. The advance of the tip of the drilling device 525 may be monitored fluoroscopically by the user, and/or the depth of drilling may be indicated by a scale printed or etched on the drilling device 525. When the path has been fully formed, the lock may be disengaged and the drilling device 525 removed from the cannula 530. The drilling device 525 can be removed by a counter rotation of the drill handle to withdraw the drill back into the cannula 530 and straighten the drill shaft in the process, after which the locking flange can be released and the drill assembly removed from the cannula 530. In an alternate embodiment, the drilling device 525 can be removed by simply unlatching it from the cannula 530 and pulling it out. This will, in turn, leave a hollow, curvilinear path through the vertebral body extending from the end of the cannula.

Figure 5C:
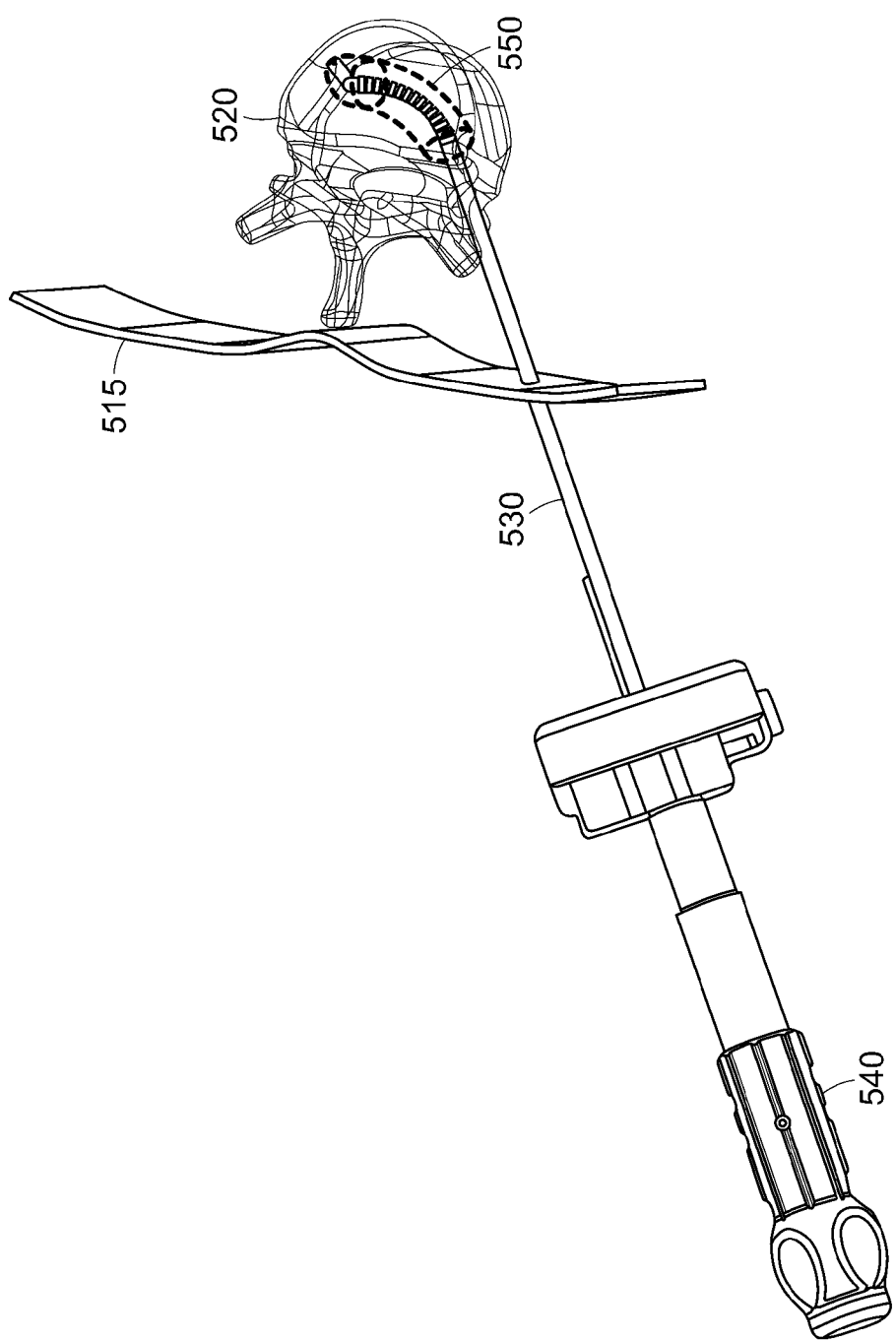
FIG. 5C is a schematic perspective view of a reamer assembly being inserted through a cannula into a vertebral body, in accordance with one embodiment of the invention.
Figure 6A:
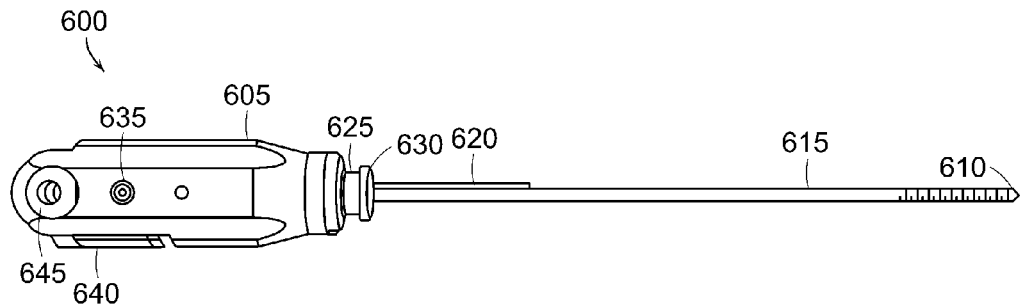
FIG. 6A is a schematic side view of a drill assembly with a lever and drill cam, in accordance with one embodiment of the invention.
Figure 6B:
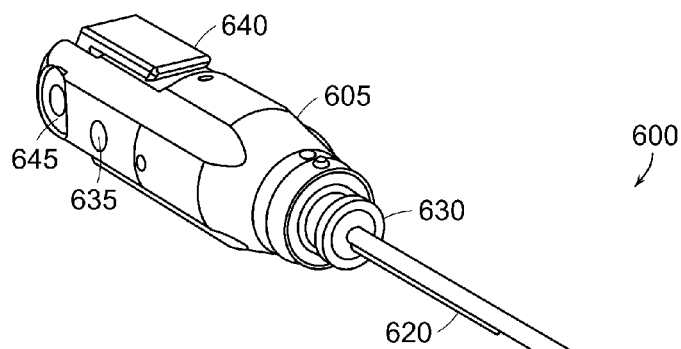
FIG. 6B is a schematic perspective view of the drill assembly of FIG. 6A.
Figure 6C:
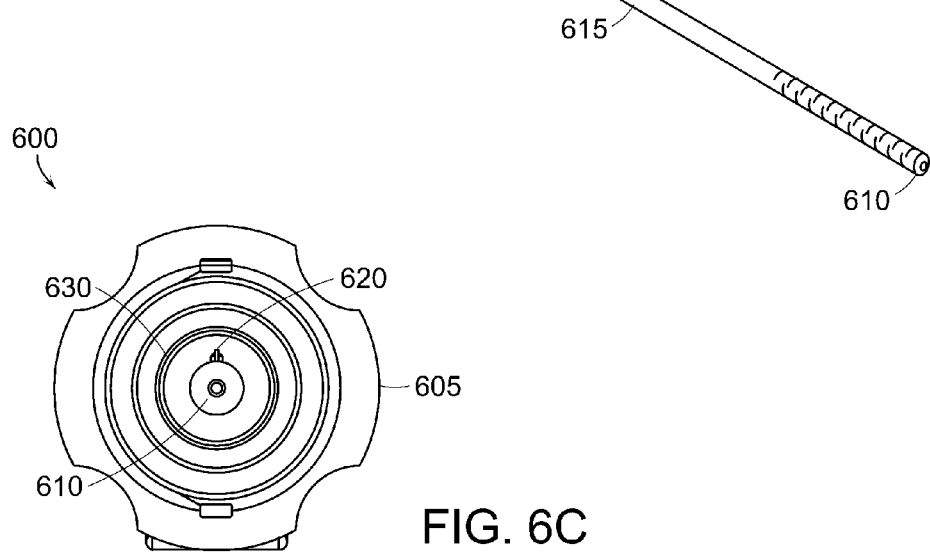
FIG. 6C is a schematic end view of the drill assembly of FIG. 6A.
Figure 6D:
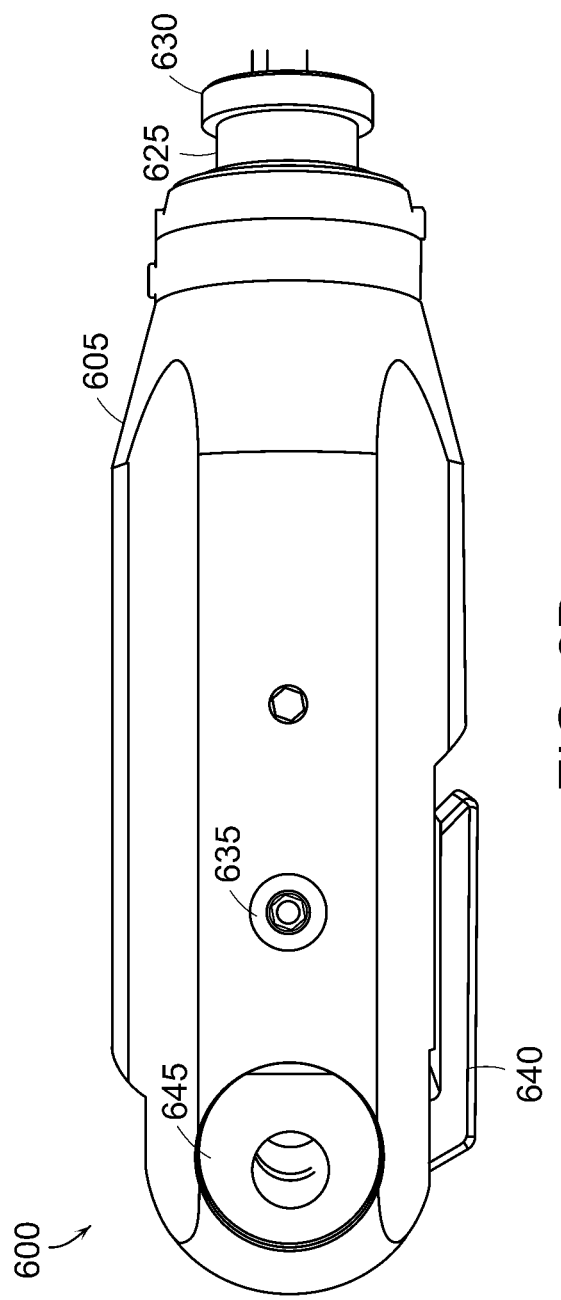
FIG. 6D is a schematic side view of the handle of the drill assembly of FIG. 6A.
Figure 6E:
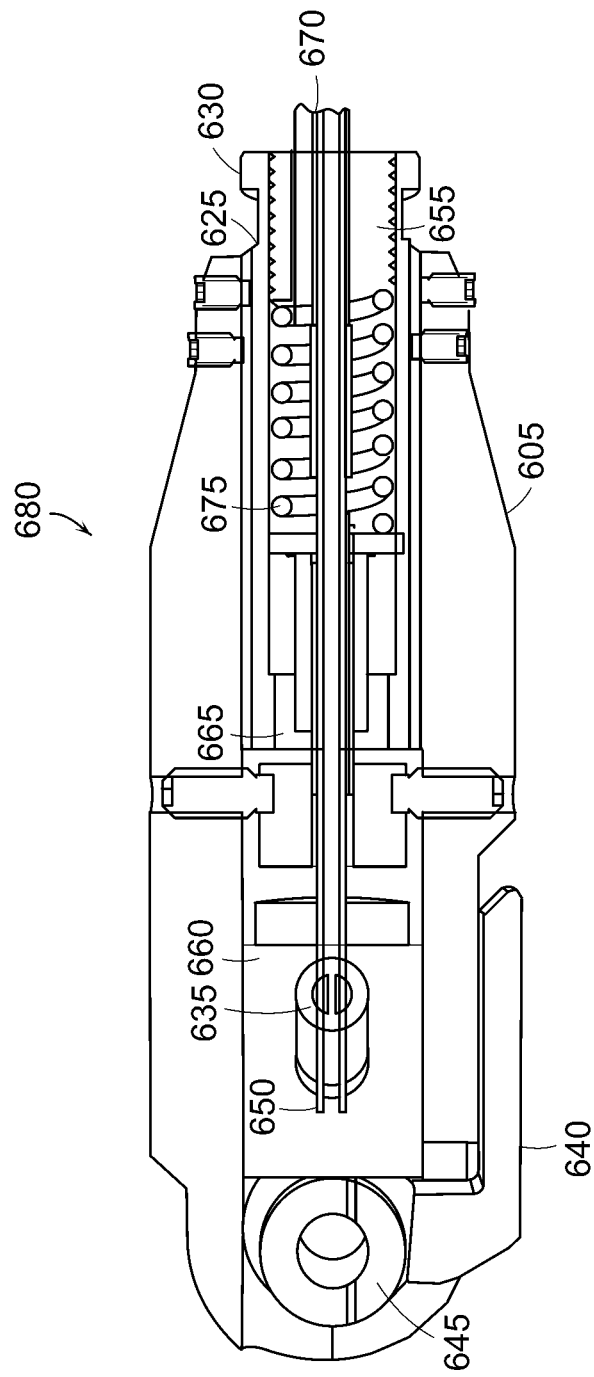
FIG. 6E is a schematic cross-sectional side view of the handle of the drill assembly of FIG. 6A through a central elongate axis of the drill assembly.

A curved reamer device can then be inserted through the cannula to enlarge the curvilinear pathway through the vertebral body created by the drilling device. An example of a reamer device 540 being inserted through a cannula 530 and into a vertebral body 520 can be seen in FIG. 5C.

The reamer device 540 can be preset to provide a desired protrusion, based on the depth of the path created by the drilling device, with reamer device 540 set to a depth that matches the drilled depth. The reamer device 540 can then be inserted through the cannula 530 to the full extent of the previously drilled cavity along the same circular path. The reamer device 540 can then be releasably locked or latched to the cannula 530. During insertion of the reamer device 540, the moveable blade of the reamer is set in an undeployed position, located substantially along the axis of the shaft, so it may easily pass through the cannula 530. In one embodiment, the position of the reamer tip can fluoroscopically confirmed within the center of the vertebral body.

The handle of the reamer device 540 can then be rotated to deploy and rotate the blade, with the reamer blade pivoting outward from the shaft and cutting a semi-sphere to a desired diameter at the distal end of the cavity, without backward movement. This therefore forms a substantially semi-spherical terminus of a cavity in the bone at the end of the curvilinear path.

Once fully deployed, the blade can rotate and translate in retrograde fashion back toward the cannula 530 along a generally helical path in response to further rotation of the handle of the reamer device 540. The blade rotating action forms a generally curvilinear elongated hole. The speed of translation and cutting is dependent on the pitch of the feedscrew mechanism in the handle. The cavity created by the reamer device 540 may be monitored fluoroscopically to determine the length of the cavity, or the length may alternatively be monitored by a printed scale on the device.

When cavity cutting is complete, the proximal end of the handle may be counter rotated to relax tension on the tether cable and allow the movement of the blade back to the closed or undeployed position. The reamer device can then be unlocked from the cannula 530 and removed. The resulting curvilinear cavity 550 is then free to have a treatment device, such as a stent and/or treatment material, such as bone cement, inserted into it.

The cannula 530 can then remain in place for insertion of other devices that will fill the cavity with medical cement. In one embodiment, these devices may include a stent and stent deployment apparatus, wherein the stent is filled with cement through the stent deployment apparatus to fill the curvilinear cavity and stabilize the vertebral body. After the cement injection procedure has been completed, the cannula 530 can be removed and the surgical incision closed.

Another embodiment of the invention can include a drill and/or reamer device including a lever and cam sub assembly or other mechanism to allow tension to be reduced in the spring assembly. This can allow the spring force providing the curvature to the drill or reamer to be reduced during insertion and/or removal of the elongated tube assembly and drill tip, thus easing the insertion and removal of the drill or reamer from the working channel during use. An example curved drill device 600 including a lever and cam sub assembly, with the distal end of the drill straightened, can be seen in FIGS. 6A through 6E.

In the embodiment shown in FIGS. 6A-6E, the curved drill device 600 can include a drive handle 605, a sharp drill tip 610 attached to a flexible torque transmitting drive shaft 650 positioned within a slotted tube assembly 615, and a handle drive assembly positioned within the handle 605. The slotted tube assembly 615 can be a spring loaded, flexible, slotted metal tube. A key component 620 can be located on the slotted tube assembly 615 to ensure that, during operation, the drill 600 is inserted and locked into the working channel, such as a hollow cannula, in the desired circumferential orientation. A drill feed nut 625 including a locking flange 630 can be threaded onto the handle drive assembly 680 located within the handle 605. with the locking flange 630 providing a locking element for releasably locking the drill 600 to a cannula. A cable retaining pin 635 can be inserted within, and keyed to, the handle 605 to provide a torque retention device to anchor the proximal end of the flexible torque transmitting drive shaft 650. The cable retaining pin 635 can then drive the shaft 650 as the handle 605 is rotated.

The handle drive assembly 680 within the handle 605 includes a feed screw 655 onto which the feed nut 625 can be threaded. The cable retaining pin 635 is located within a cam pusher assembly 660 located within the central portion of the handle 605. A band retention element 665 is used to anchor a band 670 located within the slotted tube assembly 615, and anchored at its distal end to a distal portion of the slotted tube assembly 615, to provide the force necessary to produce a curvature at the distal end of the drill 600. A compression spring 675 is positioned between the feed screw 655 and the band retention element 665 to provide a spring force to the band retention element, thereby allowing the curvature of the distal end of the drill 600 to flex.

In addition, the curved drilling device 600 includes a lever 640 attached to a drill cam 645 mounted on the proximal end of the handle 605, wherein the lever 640 pivots the drill cam 645 about a central axis upon actuation by a user. The drill cam 645 includes an eccentric inner portion that abuts against a cam pusher assembly 660 located within the central portion of the handle 605. The cam pusher assembly 660 abuts against the band retention element 665, or other intermediate element. The band retention element 665 provides a stop for the compression spring element 675 located within the central axis of the handle 605 and configured to provide a spring force to the band retention element 665, thus providing the required force to the band 650 in order to maintain the distal end of the slotted tube assembly 615 in a curved configuration.

In operation, when the lever 640 is closed against the handle 605 of the drill 600, the compression spring 675 pushes the band retention element 665 and cam pusher assembly 660 against the drill cam 645, and provides the force necessary to produce a curvature at the distal end of the drill 600. However, when the lever is pulled away from the handle 605, it pivots the drill cam 645 about its axis and, due to the eccentric configuration of the drill cam 645, forces the cam pusher assembly 660 and band retention element 665 against the spring element 675. This has the effect of compressing and foreshortening the spring element 675, thus reducing the force provided to the distal end of the slotted tube assembly 615 and therefore allowing the distal end of the slotted tube assembly 615 to be straightened with less or minimal effort.

In another embodiment of the invention, a reamer, such as any of the reaming devices described herein, could include a lever and cam sub assembly or other mechanism to compress and foreshorten a compression spring within the handle of the reamer, thus allowing the distal end of the slotted tube assembly of the reamer to be straightened with less or minimal effort.

Figure 7A:
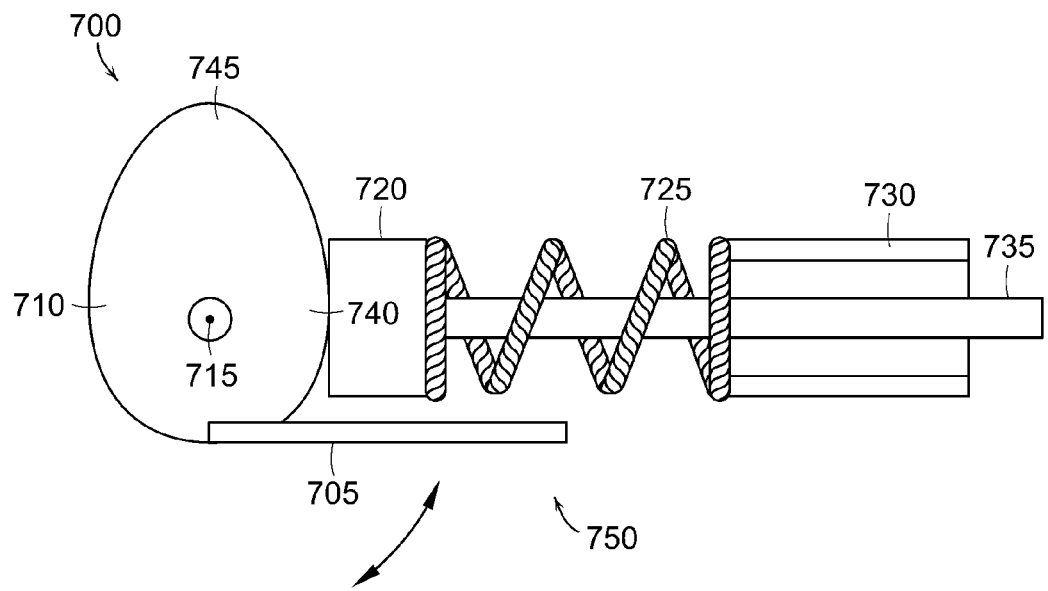
FIG. 7A is a schematic side view of a lever and cam sub assembly in a closed position, in accordance with one embodiment of the invention.
Figure 7B:
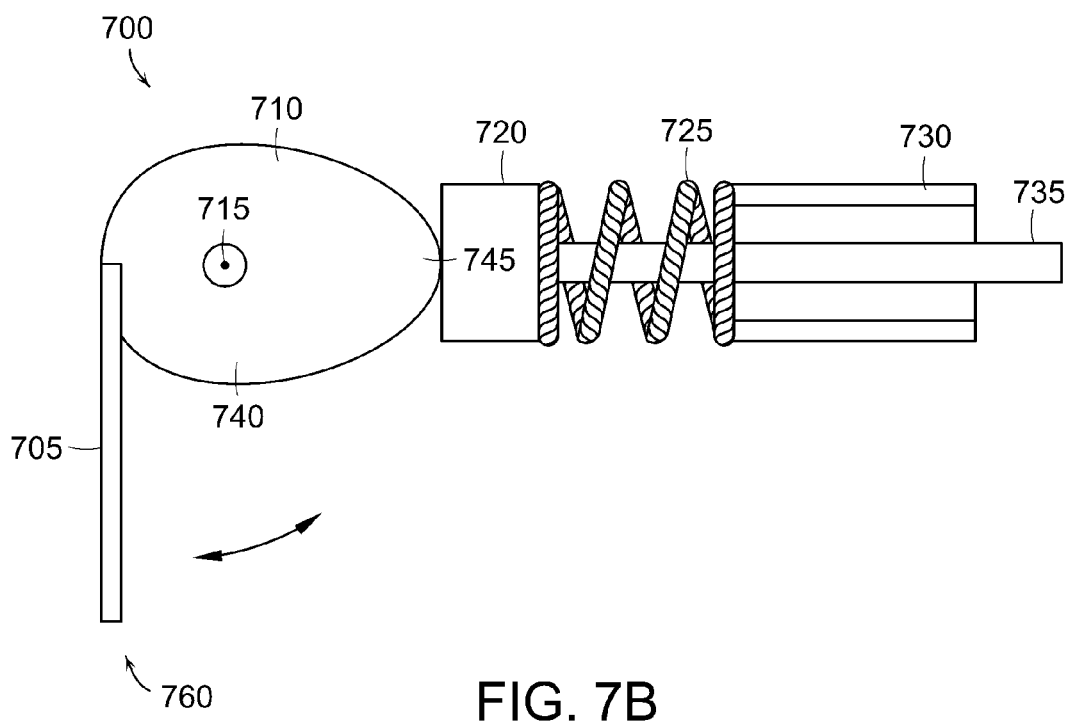
FIG. 7B is a schematic side view of the lever and cam sub assembly of FIG. 7A in an open position.

A simplified example lever and cam sub assembly 700 is shown in FIGS. 7A and 7B. In this embodiment, the lever 705 and cam 710 pivot about an axis 715. An anchoring element 720 is forced against the side of the cam 710 by a compression spring 725. A mounting element 730 holds the distal end of the compression spring 725 at a fixed position with respect to the cam axis 715. An elongate element 735 is anchored to the anchoring element 720 and extends through the center of the compression spring 725 and mounting element 730. In an alternative embodiment, the mounting element 730 may be moveable with respect to the cam axis 715, for example through a threaded screw arrangement.

In operation, when the lever 705 is in a closed position 750, as shown in FIG. 7A, the spring pushes the anchoring element 720 against the small radius side 740 of the cam 710, resulting in the anchoring element 720 providing a force holding the elongate element 735 in a first position close to the axis 715. When the lever 705 is moved to an open position 760, as shown in FIG. 7B, the large radius side 745 of the cam 710 pushes the anchoring element 720 away from the axis 715, resulting in the spring element 725 being compressed and foreshortened. As a result, the anchoring element 720 and elongate element 735 are held in a second position extending further away from the axis 715. It should be noted that the position of the lever is infinitely variable within its range of motion and can, in one embodiment, be held at any location by friction between the closed position and the open position, thus providing any intermediate position for the anchoring element 720 and the elongate element 735 and resultant intermediate force.

In one embodiment, the elongate element 735 is a band anchored at its distal end to a distal end of a slotted tube assembly for a curved drill and/or reamer device. In this embodiment, turning the lever 705 from a closed position 750 to an open position 760 will reduce the tension on the band and allow the distal end of the slotted tube assembly to be straightened more easily (i.e. without the need for a force sufficient to overcome the spring force provided by the compression spring 725). However, even when the lever 705 is in the closed position 750, by including the spring element 725, the distal end of the drill or reamer can still be straightened if it is subject to a force sufficient to overcome the spring force. As a result, the distal end of the drill or reamer is free to increase or decrease its curvature as required, if it abuts against a more solid object capable of overcoming the spring force on the distal end of the slotted tube assembly and deflecting the tip of the drill. In an alternative embodiment, the spring element 725 can be removed and the anchoring element 720 can be rotatably coupled directly to the cam 710.

In one embodiment, the anchoring element 720 can include, but is not limited to, at least one of a cam pusher assembly, a band retention element, a bushing, a flange, a handle portion, and/or any other appropriate anchoring element for a portion of a curved drilling and/or reaming device. In one embodiment, the mounting element 730 can include, but is not limited to, a feed screw, a bushing, a feed nut, a flange, a handle portion, or any other appropriate mounting element for a portion of a curved drilling and/or reaming device. The elongate element 735 can include a band, a wire, a shaft, a tube, a sheath, or any other appropriate elongate member for use in a curved drilling and/or reaming device.

In an alternative embodiment, the anchoring element 720, mounting element 730, and/or elongate element may be portions of a stent delivery device adapted to deploy a stent within a cavity created within a vertebral body, or be portions of any other appropriate devices used for the treatment of vertebral bodies or other bones.

In an alternative embodiment, the lever and cam sub assembly can be replaced by a screw assembly, a slider assembly, a trigger assembly, a rotating helix assembly, or any other appropriate assembly or mechanism for moving the anchoring element 720 with respect to the mounting element 730 to compress and foreshorten the spring element 725.

In one embodiment, the elongate element 735 can include an element providing a restoring force to straighten the distal end of a drill or reamer. This can allow the lever to provide a controllable curvature to the distal end of the drill or reamer, with the increase in angle through which the lever is turned corresponding to a decrease in the curvature of the distal end of the drill or reamer. Indicator markings on the handle of the drill can then be used to allow a user to set the distal end of the drill or reamer to any desired curvature by turning the lever to the desired location.

In alternative embodiments of the invention, any appropriate material, or combination of materials, may be used for the components described herein. Appropriate materials include, but are not limited to, stainless steel, aluminum, plastics, textiles, composite materials, or any combination thereof. The method of creating a cavity may include all, or only some of, the components described herein, depending upon the specific requirements of the system.

In further alternative embodiments of the invention, different drill and/or reamer devices can be used to create the cavity. These may include one or more blades or drill bits, looped or otherwise configured wires, or other drilling, boring, or reaming devices. The blades may be of any appropriate shape and configuration.

In one embodiment of the invention, a fiber optic camera device may be inserted into the cannula to provide images of the curvilinear pathway and cavity to a physician at any point during the procedure. The camera may also provide diagnostic information that may be used when determining the required size and shape of the cavity being created.

In alternative embodiments of the invention, the arc of the drilling device and/or reamer device may be selected to provide any shape of curvilinear cavity. Different arcs may be provided by selection of different tools, with each tool being set to provide one specific arc. Alternatively an individual device may be adaptably configured to provide an arc of any required curvature. In further alternative embodiments, drill and/or reamer devices can be used to create cavities within other bones of a body or within any other structural element, such as, but not limited to, spinal disc tissue. As a result, the methods and apparatus described herein can be used in the treatment of other bones within a body, such as, but not limited to, broken or otherwise damaged limb bones, or for disc fusion techniques.

It should be understood that alternative embodiments, and/or materials used in the construction of embodiments, or alternative embodiments, are applicable to all other embodiments described herein.

The invention may be embodied in other specific forms without departing from the spirit or essential characteristics thereof. The foregoing embodiments, therefore, are to be considered in all respects illustrative rather than limiting the invention described herein. Scope of the invention is thus indicated by the appended claims, rather than by the foregoing description, and all changes that come within the meaning and range of equivalency of the claims are intended to be embraced therein.

The invention claimed is:

1. A method of forming a curvilinear void in bony structure, the method comprising the steps of:
   accessing a bony structure with a cannula;
   inserting a distal end of a drill device through the cannula and into the bony structure, the drill device comprising a flexible drill shaft assembly, wherein the flexible drill shaft assembly comprises a handle having a rotatable element and a handle spring, a drill shaft affixed to a feed screw, a compression spring, a band retention element, and a lever and cam sub assembly comprising a drill cam and a cam pusher assembly for varying a force used to apply a curvature to a distal end of the flexible drill shaft assembly, wherein the drill cam comprises an outer surface wall and an inner surface wall, wherein the outer surface wall is in contact with the cam pusher assembly, and the band retention element is positioned outside of the drill cam, wherein the lever has a first position pointing toward the compression spring that is against the handle and a second position that is away from the handle, wherein when the lever is in the second position away from the handle the compression spring is under greater compression than when the lever is in the first position against the handle, further wherein when the lever is in the second position the drill cam is pivoted and forces the cam pusher assembly toward the compression spring;
   manipulating the distal end of the drill device to create a curvilinear void in the bony structure; and
   removing the distal end of the drill device from the cannula, wherein the flexible drill shaft assembly further comprises a sharp cutting tip, a band coupled at a distal end proximate to the cutting tip and at a proximal end to the compression spring, a flexible rotatable drive shaft coupled to the tip, and a flexible, moveable and non-rotatable housing.

2. The method of claim 1, wherein the step of manipulating of the distal end of the drill device comprises a simultaneous rotation and curvilinear translation of the distal end of the drill device.

3. The method of claim 1, wherein the cannula is straight.

4. The method of claim 1, wherein the step of manipulating the distal end of the drill device comprises inducing a curvature in the distal end of the flexible drill shaft assembly.

5. The method of claim 1, further comprising the step of:
moving the lever to the first position to reduce the force on the distal end of the flexible drill shaft assembly prior to removing the distal end of the drill device from the cannula.

6. The method of claim 1, wherein the flexible drill shaft assembly further comprises a sharp cutting tip, a band coupled at a distal end proximate to the cutting tip and at a proximal end to the compression spring, a flexible rotatable drive shaft coupled to the tip, and a flexible, moveable and non-rotatable housing.

7. The method of claim 1, wherein the drilling device further comprises a locking feature.

8. The method of claim 7, further comprising the steps of:
locking the drill device into the cannula using the locking feature prior to forming the void; and
unlocking the drill device from the cannula after forming the void and prior to removing the distal end of the drill device.

9. The method of claim 1, wherein the drill device is manipulated in response to a rotation of an element at a proximal end of the drill device.

10. The method of claim 1, wherein the second position is substantially perpendicular to the first position.

11. The method of claim 1, wherein the drill cam comprises a first outer radius and a second outer radius that is different than the first outer radius.

12. The method of claim 11, wherein the second outer radius is larger than the first outer radius.

13. The method of claim 12, wherein the drill cam has a first end and a second end, the first end includes the second outer radius and a portion of the lever is attached to the second end of the drill cam.

14. The apparatus of claim 1, wherein the handle includes a retaining pin and a drive shaft, wherein the retaining pin anchors a proximal end of the drive shaft to the handle.

15. The apparatus of claim 14, wherein the retaining pin is positioned between the cam and the band retention element.

16. The apparatus of claim 1, wherein the handle includes a feed nut threaded onto the feed screw, the compression spring is positioned between the feed screw and the band retention element, and the feed nut has a locking flange configured to releasably lock the handle to the cannula.

17. The apparatus of claim 1, wherein the flexible shaft assembly includes a key component located on an outer surface of a slotted tube, wherein the key component slidably mates with a slot in the cannula to lock the orientation of the drill device relative to the cannula.

18. A method of forming a curvilinear void in bony structure, the method comprising the steps of:
accessing a bony structure with a cannula;
inserting a distal end of a drill device into the bony structure, the drill device comprising a flexible drill shaft assembly, wherein the flexible drill shaft assembly comprises a handle having a rotatable element and a handle spring, a drill shaft affixed to a compression spring, a band retention element, and a lever and cam sub assembly for varying a force used to apply a curvature to a distal end of the flexible drill shaft assembly, wherein the cam sub assembly comprises a drill cam and a cam pusher assembly, wherein the drill cam comprises an outer surface wall and an inner surface wall, wherein the outer surface wall is in contact with the cam pusher assembly, and the band retention element is positioned outside of the drill cam, wherein the lever has a first position pointing toward the compression spring that is against the handle and a second position that is away from the handle, wherein when the lever is in the second position away from the handle the compression spring is under greater compression than when the lever is in the first position against the handle, further wherein when the lever is in the second position the drill cam is pivoted and forces the cam pusher assembly toward the compression spring; and
manipulating the distal end of the drill device to create a curvilinear void in the bony structure,
wherein the flexible drill shaft assembly includes a key component located on an outer surface of a slotted tube, wherein the key component slidably mates with a slot in the cannula to lock the orientation of the drill device relative to the cannula.

19. The method of claim 18, wherein the force at the first position is less than the second position of the lever.

20. The method of claim 18, wherein the force used to apply a curvature is applied to the distal end of the flexible shaft assembly by a band connected at a proximal end to the band retention element and at a distal portion of the flexible drill shaft assembly.

* * * * *